United States Patent
Kallmes et al.

(10) Patent No.: US 11,229,466 B2
(45) Date of Patent: Jan. 25, 2022

(54) BONE EXPANSION SYSTEMS AND METHODS

(71) Applicant: KyphEZE, Inc., Rochester, MN (US)

(72) Inventors: David F. Kallmes, Rochester, MN (US); Waleed Brinjikji, Rochester, MN (US)

(73) Assignee: KyphEZE, Inc., Rochester, MN (US)

( * ) Notice: Subject to any disclaimer, the term of this patent is extended or adjusted under 35 U.S.C. 154(b) by 339 days.

(21) Appl. No.: 16/542,687

(22) Filed: Aug. 16, 2019

(65) Prior Publication Data

US 2019/0365445 A1 Dec. 5, 2019

Related U.S. Application Data

(63) Continuation-in-part of application No. 15/744,479, filed on Jan. 12, 18, now Pat. No. 10,398,485.

(51) Int. Cl.
| | |
|---|---|
| *A61B 17/58* | (2006.01) |
| *A61B 17/60* | (2006.01) |
| *A61F 2/00* | (2006.01) |
| *A61B 17/88* | (2006.01) |
| *A61M 5/00* | (2006.01) |

(Continued)

(52) U.S. Cl.
CPC ...... *A61B 17/8811* (2013.01); *A61B 17/8819* (2013.01); *A61M 5/007* (2013.01); *A61M 25/1002* (2013.01); *A61B 2017/00557* (2013.01); *A61M 2025/1075* (2013.01)

(58) Field of Classification Search
CPC combination set(s) only.
See application file for complete search history.

(56) References Cited

U.S. PATENT DOCUMENTS

| | | | |
|---|---|---|---|
| 5,320,605 | A | 6/1994 | Sahota |
| 5,334,146 | A | 8/1994 | Ozasa |

(Continued)

FOREIGN PATENT DOCUMENTS

| | | |
|---|---|---|
| CA | 2333761 C | 12/1999 |
| EP | 0836435 B1 | 9/2004 |

(Continued)

OTHER PUBLICATIONS

PCT International Search Report and Written Opinion in International Application No. PCT/US2016/27300, dated Jul. 15, 2016, 12 pages.

(Continued)

*Primary Examiner* — Sameh R Boles
(74) *Attorney, Agent, or Firm* — Wesley E. Schwie, Esq.; Gallium Law

(57) ABSTRACT

A needle-mounted balloon system can include a cannula and a stylet. The cannula may include a handle and an outer sheath, and the outer sheath may be configured to retract and expose at least a portion of an expandable member. The stylet may include a stylet needle and a sharp distal tip portion. The stylet needle may be used to insert the system into a body structure, after which the stylet may be disengaged from the cannula. The expandable member may then be exposed and inflated to create a space in the body structure. Filler material may be injected through the cannula to the open space in an effort to stabilize an injured or otherwise destabilized portion of the body structure.

21 Claims, 19 Drawing Sheets

(51) Int. Cl.
*A61M 25/10* (2013.01)
*A61B 17/00* (2006.01)

(56) References Cited

U.S. PATENT DOCUMENTS

| | | | |
|---|---|---|---|
| 5,348,538 | A | 9/1994 | Wang |
| 5,707,357 | A | 1/1998 | Mikhail |
| 5,766,151 | A | 6/1998 | Valley |
| 6,066,154 | A | 5/2000 | Reiley |
| 6,241,734 | B1 | 6/2001 | Scribner |
| 6,296,660 | B1 | 10/2001 | Roberts |
| 6,544,224 | B1 | 4/2003 | Steese-Bradley |
| 6,607,544 | B1 | 8/2003 | Boucher |
| 6,613,054 | B2 | 9/2003 | Scribner |
| 6,648,854 | B1 | 11/2003 | Patterson |
| 6,663,647 | B2 | 12/2003 | Reiley |
| 6,773,447 | B2 | 8/2004 | Laguna |
| 6,951,569 | B2 | 10/2005 | Nohilly |
| 7,011,646 | B2 | 3/2006 | Blankenship |
| 7,175,607 | B2 | 2/2007 | Lim |
| 7,261,720 | B2 | 8/2007 | Stevens |
| 7,691,080 | B2 | 4/2010 | Seward |
| 7,708,742 | B2 | 5/2010 | Scribner |
| 7,753,875 | B2 | 7/2010 | Burton |
| 7,951,111 | B2 | 5/2011 | Drasler |
| 8,221,349 | B2 | 7/2012 | Auyoung |
| 8,262,609 | B2 | 9/2012 | Sapida |
| 8,827,951 | B2 | 9/2014 | Besser |
| 8,961,525 | B2 | 2/2015 | Donovan |
| 9,126,035 | B2 | 9/2015 | Valoir |
| 9,149,318 | B2 | 10/2015 | Druma |
| 9,295,510 | B2 | 3/2016 | Auyuong |
| 9,326,799 | B2 | 5/2016 | O'Halloran |
| 9,480,824 | B2 | 11/2016 | Kaiser |
| 9,554,840 | B2 | 1/2017 | Druma |
| 9,592,119 | B2 | 3/2017 | Tilson |
| 9,668,796 | B2 | 6/2017 | Druma |
| 9,956,384 | B2 | 5/2018 | Charlebois |
| 10,105,519 | B2 | 10/2018 | Chanduszko |
| 2002/0177866 | A1 | 11/2002 | Weikel |
| 2005/0131268 | A1 | 6/2005 | Talmadge |
| 2007/0010845 | A1 | 1/2007 | Gong |
| 2007/0244501 | A1 | 10/2007 | Horn |
| 2008/0058828 | A1 | 3/2008 | Reiley |
| 2008/0065139 | A1 | 3/2008 | Scribner |
| 2008/0312637 | A1* | 12/2008 | Miller ............... A61M 25/10 604/512 |
| 2009/0299282 | A1 | 12/2009 | Lau |
| 2010/0076437 | A1 | 3/2010 | Tilson |
| 2011/0251615 | A1 | 10/2011 | Truckai |
| 2012/0016371 | A1 | 1/2012 | O'Halloran |
| 2012/0259375 | A1 | 10/2012 | Druma |
| 2014/0012330 | A1 | 1/2014 | Johnson |
| 2014/0257311 | A1 | 9/2014 | Druma |
| 2019/0110826 | A1 | 4/2019 | Goshayeshgar |

FOREIGN PATENT DOCUMENTS

| | | |
|---|---|---|
| WO | 1992011892 A1 | 7/1992 |
| WO | 2009149108 A1 | 12/2009 |

OTHER PUBLICATIONS

PCT International Preliminary Report on Patentability in International Application No. PCT/US2016/27300, dated Jan. 16, 2018, 7 pages.

* cited by examiner

BONE EXPANSION SYSTEMS AND METHODS

CROSS REFERENCE TO RELATED APPLICATION

This application is a continuation-in-part of U.S. application Ser. No. 15/744,479; filed on Jan. 12, 2018; and entitled BONE EXPANSION DEVICES AND METHODS; the entire contents of which are incorporated herein by reference.

BACKGROUND

Field

The invention relates generally to medical devices and methods of use. Embodiments of the invention include devices for performing procedures involving creating space within a body structure for therapeutic purposes. For example, this invention relates to orthopedic devices and methods for creating space within bone, and for injecting a filler material such as cement into the space to strengthen, repair, or otherwise enhance the bone structure.

Description of Art

Cementoplasty pertains to percutaneous procedures including vertebroplasty, kyphoplasty, osteoplasty, and sacroplasty. In general, bone packing with cement aims to treat or prevent vertebral and extraspinal pathological fractures and relieve pain in patients with conditions such as osteoporosis and bone metastases.

Vertebroplasty and kyphoplasty are minimally invasive procedures for the treatment of painful vertebral compression fractures, which are fractures involving the vertebral bodies that make up the spinal column. In vertebroplasty, physicians use image guidance to inject a cement mixture into the fractured bone through a hollow needle. In kyphoplasty, a balloon is first inserted into the fractured bone through the hollow needle and then inflated to create a cavity or space. The cement is injected into the cavity once the balloon is removed.

Percutaneous osteoplasty, the injection of bone cement into a bone lesion refractory to conventional therapy (e.g., radiotherapy, chemotherapy, and narcotic analgesia), is performed to provide immediate bone structure consolidation, to reduce the risk of a pathological fracture, to achieve pain regression, and to improve mobility.

SUMMARY

This document provides devices and methods for creating space within a body structure for therapeutic purposes. For example, this document provides orthopedic devices and methods for creating space within bone, and for injecting a filler material such as cement into the space to strengthen, repair, or otherwise enhance the bone structure.

In one implementation, a needle-mounted balloon system includes a cannula and a stylet that is engageable with the cannula. The cannula includes a cannula hub, a cannula tube portion extending distally from the cannula hub and defining a lumen therethrough, and an expandable member coupled to the cannula tube portion. The expandable member is reconfigurable between a diametrically contracted configuration and a diametrically expanded configuration. The stylet includes a stylet hub and a stylet needle extending distally from the stylet hub. The stylet needle is slidably disposable within the lumen of the cannula tube portion. When the stylet is fully engaged with the cannula, a sharp distal tip portion of the stylet needle extends distally beyond the cannula tube portion.

Such a needle-mounted balloon system may optionally include one or more of the following features. The needle-mounted balloon system may also include an inflation tube coupled with the cannula and in fluid communication with the expandable member. The inflation tube may be coupled with the cannula hub. The cannula tube portion may define an inflation lumen that is in fluid communication with the expandable member and the inflation tube. In some embodiments, the expandable member is expandable only when the stylet is engaged with the cannula. In some embodiments, the expandable member is expandable when the stylet is engaged with the cannula and when the stylet is disengaged from the cannula. The needle-mounted balloon system may also include a connection member coupled with the cannula hub and in fluid communication with the lumen. The expandable member is a balloon device in various embodiments. The balloon device may be diametrically symmetrical. The balloon device may be diametrically asymmetrical. The needle-mounted balloon system may also include a second expandable member coupled to the cannula tube portion. In some embodiments, a distal-most portion of the cannula tube portion has a larger outer diameter than an outer diameter of the expandable member while the expandable member is in the diametrically contracted configuration.

In another implementation, a method for creating a space in a body structure and injecting a filler material into the space includes: (i) inserting a distal end portion of a needle-mounted balloon system into the body structure, (ii) reconfiguring the expandable member of the needle-mounted balloon system from the diametrically contracted configuration to the diametrically expanded configuration while the expandable member is in the body structure, (iii) reconfiguring the expandable member from the diametrically expanded configuration to the diametrically contracted configuration such that an open space is created in the body structure, and (iv) injecting a filler material into the open space.

Such a method for creating a space in a body structure and injecting a filler material into the space may optionally include one or more of the following features. The method may also include, prior to the injection of the filler material, removing the stylet from engagement with the cannula. In some embodiments, the body structure is bone. In some embodiments, the filler material is bone cement.

Particular embodiments of the subject matter described in this document can be implemented to realize one or more of the following advantages. In some embodiments, the devices and methods described herein provide enhanced ease-of-use in comparison to the devices and methods presently available for creating space within a body structure. For example, the devices and methods described herein may require fewer steps and fewer physical components. In addition to ease-of-use, the devices and methods described herein may reduce the amount of time required to perform a procedure. Further, with fewer components and a reduction in procedural times, a cost savings may be attained using the devices and methods provided herein. In use, the balloon device of the devices provided herein can be advantageously fully or partially inflated during the injection of filler material. Hence, the balloon device can be used to help achieve a desired placement of the filler material in the body cavity. In some embodiments, various conditions can be treated in a minimally invasive fashion using the devices and methods provided herein. Such minimally invasive techniques can reduce recovery times, patient discomfort, and treatment costs.

In some embodiments, a needle-mounted balloon system comprises a cannula and a stylet that is engageable with the cannula. The cannula may comprise a handle, a cannula hub coupled within a housing of the handle, a cannula tube portion extending distally from the cannula hub, the cannula tube portion defining a lumen therethrough, and an expandable member coupled to the cannula tube portion, where the expandable member is reconfigurable between a diametrically contracted configuration and a diametrically expanded configuration. The stylet may comprise a stylet hub detachably coupled to the handle and a stylet needle extending distally from the stylet hub, where the stylet needle may be slideably disposable within the lumen of the cannula tube portion. In some embodiments, when the stylet is fully engaged with the cannula, a sharp distal tip portion of the stylet needle extends distally beyond the cannula tube portion. The expandable member may be expandable when the stylet is disengaged from the cannula.

The needle-mounted balloon system may also include an outer sheath slideaby coupled to the cannula tube portion, wherein the expandable member is located between the outer sheath and the cannula tube portion. In some embodiments, the system includes an inflation port and an injection port both disposed on the cannula hub, where the inflation port is in fluid communication with the expandable member and the injection port is in fluid communication with the lumen of the cannula tube portion. The outer sheath may be configured to retract and expose at least a portion of the expandable member when the stylet is disengaged from the cannula.

In some embodiments, a distal-most portion of the cannula tube portion has a larger outer diameter than an outer diameter of the expandable member when the expandable member is in the diametrically contracted configuration. The distal-most portion of the cannula tube portion may define an outer diameter of about 0.134 inches.

In some embodiments, an internal portion of the stylet needle is hollow. Alternatively, the internal portion of the stylet needle may be solid. The distal tip portion of the stylet needle may extend beyond the distal-most portion of the cannula tube portion a distance of about 0.24 inches. In some embodiments, the needle-mounted balloon system defines a length of about 7 inches from the distal tip portion of the stylet needle to a proximal end of the handle.

The expandable member may be a balloon that is diametrically symmetrical. Alternatively, the expandable member may be a balloon that is diametrically asymmetrical. In some embodiments, the expandable member is a balloon comprising dual layers, wherein each layer is a 90AE balloon and the dual layers are coupled together via heat bonding.

In some embodiments, a method for creating a space in a body structure and injecting a filler material into the space comprises inserting a distal end portion of a needle-mounted balloon system into the body structure, wherein the needle-mounted balloon system comprises a cannula comprising a handle, a cannula hub coupled within a housing of the handle, a cannula tube portion extending distally from the cannula hub, the cannula tube portion defining a lumen therethrough, and an expandable member being reconfigurable between a diametrically contracted configuration and a diametrically expanded configuration. The needle-mounted balloon system may further comprise a stylet that is engageable with the cannula, where the stylet may comprise a stylet hub detachably coupled to the handle and a stylet needle extending distally from the stylet hub, wherein the stylet needle is slideably disposable within the lumen of the cannula tube portion, wherein, when the stylet is fully engaged with the cannula, a sharp distal tip portion of the stylet needle extends distally beyond the cannula tube portion, and wherein the expandable member is expandable when the stylet is disengaged from the cannula.

The method may further comprise reconfiguring the expandable member from the diametrically contracted configuration to the diametrically expanded configuration while the expandable member is in the body structure. In many embodiments, the method further comprises reconfiguring the expandable member from the diametrically expanded configuration to the diametrically contracted configuration such that an open space remains in the body structure, and injecting the filler material into the open space. The method may further comprise retracting an outer sheath coupled to an external portion of the cannula in order to at least partially expose the expandable member. In some embodiments, prior to retracting the outer sheath, the method comprises retracting the stylet needle through the lumen of the cannula.

In many embodiments, the body structure is bone and the filler material is bone cement. The stylet needle may be retracted by turning a knob on the handle of the needle-mounted balloon system, where the knob is coupled to a proximal end of the stylet. In some embodiments, turning the knob comprises a quarter turn. The outer sheath may be retracted by moving at least one tab of the handle in a proximal direction, wherein the at least one tab is exposed upon turning the knob, and the at least one tab is coupled to the outer sheath. In some embodiments, reconfiguring the expandable member from the diametrically contracted configuration to the diametrically expanded configuration occurs in response to injecting at least one of saline and contrast dye into an inflation port disposed on the cannula hub.

The details of one or more embodiments of the invention are set forth in the accompanying drawings and the description herein. Other features, objects, and advantages of the invention will be apparent from the description and drawings, and from the claims.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments.

FIG. 1A is a cross-sectional view of an example cannula of the needle-mounted balloon system of FIG. 1. The cannula includes an inflation lumen and a lumen for a stylet.

FIG. 1B is an enlarged view of the distal end portion of the needle-mounted balloon system of FIG. 1.

DETAILED DESCRIPTION

Figure 1:
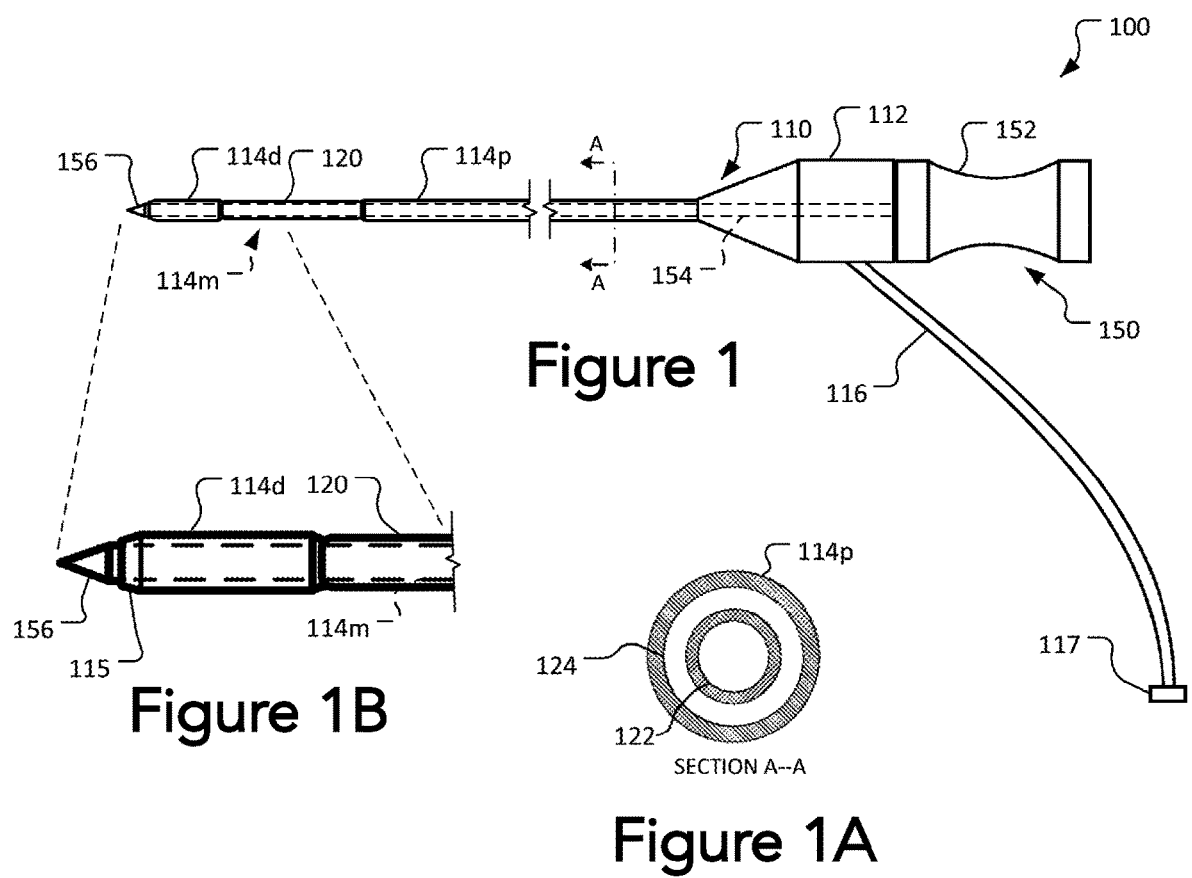
FIG. 1 is a side view of an example needle-mounted balloon system for bone expansion in accordance with some embodiments provided herein. The needle-mounted balloon system is shown with its balloon in a contracted/deflated configuration.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The terms "expandable member" and "balloon" may be used interchangeably in this disclosure.

LIST OF REFERENCE NUMBERS

100—needle mounted balloon system
110—cannula
112—cannula hub
114—cannula tube portion
114*d*—distal cannula tube portion
114*m*—mid-body cannula tube portion
114*p*—proximal cannula tube portion
115—distal leading-end
116—inflation tube
117—connection
118—connection member
120—expandable member
122—main lumen
124—one or more inflation lumens
126—handle
128—handle housing
130—outer sheath
132—inflation port
134—injection port
136—a portion of the expandable member
138—outer diameter (of distal-most portion)
140—outer diameter (of expandable member)
142—proximal end (of handle)
144—balloon
146—diametrically contracted configuration
148—diametrically expanded configuration
150—stylet
152—stylet hub
154—needle
156—distal tip portion
400—needle-mounted balloon system
410—cannula
414*d*—distal cannula tube portion
414*m*—mid-body cannula tube portion
414*p*—proximal cannula tube portion
416—inflation tube
417—connection
420—expandable member
450—stylet
452—stylet hub
454—needle
456—distal tip portion 600—needle-mounted balloon system
610—cannula
614d—distal cannula tube portion
614m—mid-body cannula tube portion
614p—proximal cannula tube portion
616—inflation tube
617—connection
620—expandable member
650—stylet
652—stylet hub
654—mid-body portion
656—distal end portion
657—sealing member(s)

This document provides devices and methods for creating space within a body structure for therapeutic purposes. For example, this document provides orthopedic devices and methods for creating space within bone, and for injecting a filler material such as cement into the space to strengthen, repair, or otherwise enhance the bone structure.

Traditional systems for creating space within bone include a cannula and a separate balloon device that can be inserted via the cannula. First, the cannula is inserted so that its distal tip is located at a target area. Then the balloon device is introduced through a lumen of the cannula. After creating or enlarging a space by inflating the balloon device, the balloon device is then removed. Subsequently, a filler material, such as bone cement, is injected into the space via the cannula.

The devices and methods provided herein significantly improve upon the traditional systems and methods for creating space within a body (such as bone) by combining the cannula and balloon device into a single component. In addition, the devices and methods provided herein include an outer sheath slideably coupled to the cannula over the balloon, such that the balloon is protected beyond what was previously possible with existing devices. Accordingly, as described further below, the devices are easier and less time-consuming for a clinician to use. It should be understood that while the devices provided herein may be termed as "needle-mounted balloon systems," the devices can also be considered "cannula-mounted balloon systems."

Referring to FIG. 1, an example needle-mounted balloon system 100 for bone expansion includes a cannula 110 and a stylet 150. Stylet 150 is slidably received within a lumen of the cannula 110. When stylet 150 is fully engaged with cannula 110, a sharp distal tip portion 156 of stylet 150 projects distally beyond a distal cannula tube portion 114d of cannula 110.

Figure 3:
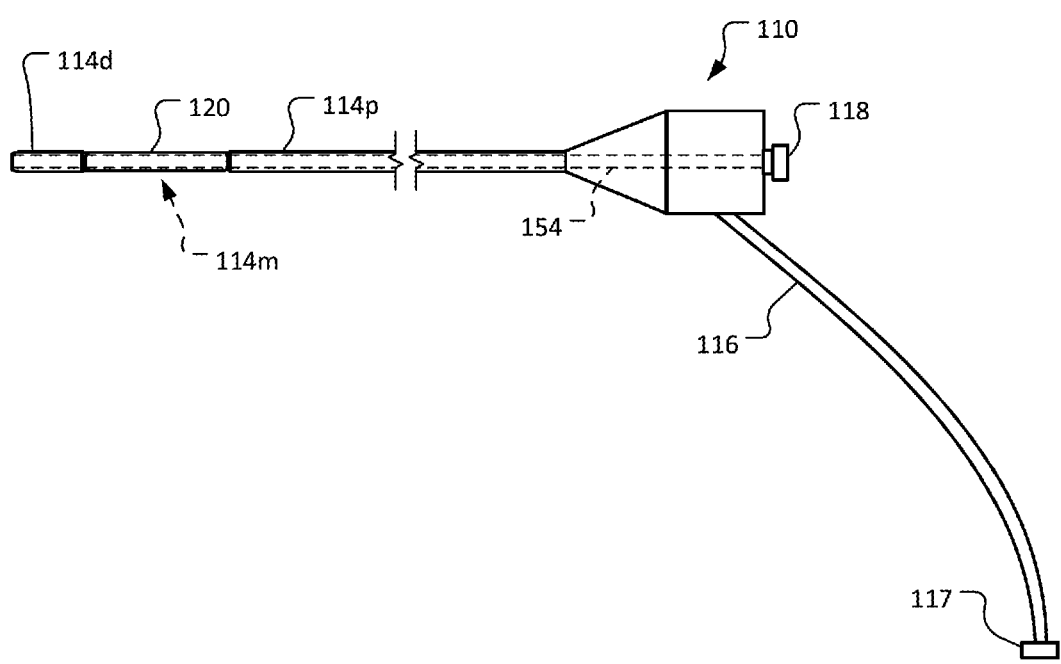
FIG. 3 is a side view of the example needle-mounted balloon system for bone expansion of FIG. 1. The needle-mounted balloon system is shown with its stylet removed.

In the depicted embodiment, cannula 110 includes a cannula hub 112, a proximal cannula tube portion 114p, a mid-body cannula tube portion 114m, an expandable member 120, distal cannula tube portion 114d, an inflation tube 116, and a connection member 118 (refer to FIG. 3). Cannula hub 112 is disposed at or near a proximal end of cannula 110. Proximal cannula tube portion 114p is coupled with cannula hub 112, and extends distally from cannula hub 112.

Referring also to FIG. 1A, proximal cannula tube portion 114p defines a main lumen 122 in which stylet 150 is slidably received. Additionally, in some embodiments proximal cannula tube portion 114p defines or includes one or more inflation lumens 124 (e.g., in the wall of proximal cannula tube portion 114p) through which an inflation media used for inflating expandable member 120 can flow. It should be understood that any of many different multi-lumen cannula designs can be used for proximal cannula tube portion 114p without departing from the scope of the disclosure. Alternatively, or additionally, in some embodiments such an inflation lumen may be provided by a separate tube.

In some embodiments, inflation tube 116 is also coupled with cannula hub 112. Alternatively, inflation tube 116 can bypass cannula hub 112 and be directly connected to proximal cannula tube portion 114p, the aforementioned inflation lumen, or expandable member 120. In the depicted embodiment, inflation tube 116 is in fluid communication with expandable member 120 via cannula hub 112 and/or the aforementioned inflation lumen.

When a source of inflation fluid (e.g., saline, radiographic contrast material, or a combination of both) is coupled with inflation tube 116 (e.g., via a connection 117), expandable member 120 can be inflated or deflated by pressurizing or depressurizing the source of inflation fluid. In some cases (without limitation), a syringe is used as the source of the inflation fluid. In some embodiments, a stopcock valve or other type of fluid control device can be used in conjunction with, or as an alternative to, connection 117. In some embodiments, connection 117 is a luer or luer-lock fitting.

Proximal cannula tube portion 114p extends distally from cannula hub 112. In some embodiments, proximal cannula tube portion 114p is metallic (e.g., stainless steel, nitinol, and the like). In some embodiments, proximal cannula tube portion 114p is made of a suitable biocompatible polymeric material. Proximal cannula tube portion 114p may be sized to any suitable length and diameter. For example, in some embodiments the outer diameter of proximal cannula tube portion 114p (without limitation) is in a range from about 2.4 mm to about 4.0 mm, or about 2.0 mm to about 3.0 mm, or about 1.5 mm to about 3.5 mm, or about 1.0 mm to about 2.5 mm, or any other suitable size. In some embodiments, the length of proximal cannula tube portion 114p (without limitation) is in a range from about 2.0 cm to about 4.0 cm, or about 3.0 cm to about 5.0 cm, or about 4.0 cm to about 6.0 cm, or about 5.0 cm to about 7.0 cm, or about 6.0 cm to about 8.0 cm, or about 7.0 cm to about 9.0 cm, or about 8.0 cm to about 10.0 cm, about 10.0 cm to about 15.0 cm, about 15.0 cm to about 20.0 cm, or greater than 20 cm, or any other suitable length.

Mid-body cannula tube portion 114m extends distally from proximal cannula tube portion 114p. In some embodiments, expandable member 120 is mounted on or around mid-body cannula tube portion 114m. Mid-body cannula tube portion 114m may have a smaller outer diameter than proximal cannula tube portion 114p, in some embodiments. In some such embodiments, the combined outer diameter of expandable member 120 (in its contracted configuration as shown) on mid-body cannula tube portion 114m is about the same diameter as, or a little smaller than, the outer diameter of proximal cannula tube portion 114p. In some such embodiments, the combined outer diameter of expandable member 120 (in its contracted configuration as shown) on mid-body cannula tube portion 114m is larger than the outer diameter of proximal cannula tube portion 114p.

In the depicted embodiment, distal cannula tube portion 114d extends distally from mid-body cannula tube portion 114m. Distal cannula tube portion 114d is optional. In some embodiments, no distal cannula tube portion 114d is included as part of needle-mounted balloon system 100. Instead, expandable member 120 and/or mid-body cannula tube portion 114m may be the distal-most portion of needle-mounted balloon system 100. In some embodiments, such as the depicted embodiment, that include distal cannula tube portion 114d, distal cannula tube portion 114d may have a length in a range of about 1.0 mm to about 6.0 mm, or about 4.0 mm to about 9.0 mm, or about 7.0 mm to about 12.0 mm, or about 10.0 mm to about 15.0 mm, or about 13.0 mm to about 18.0 mm, or about 16.0 mm to about 21.0 mm, or about 19.0 mm to about 24.0 mm, or about 22.0 mm to about 25.0 mm, or greater than 25.0 mm (e.g., about 3 cm, about 4 cm, about 5 cm, and the like). In some embodiments the outer diameter of distal cannula tube portion 114d (without limitation) is in a range from about 2.4 mm to about 4.0 mm, or about 2.0 mm to about 3.0 mm, or about 1.5 mm to about 3.5 mm, or about 1.0 mm to about 2.5 mm, or any other suitable size. While in some embodiments the outer diameter of distal cannula tube portion 114d is the same as the outer diameter of proximal cannula tube portion 114p, in some embodiments the outer diameters of distal cannula tube portion 114d and proximal cannula tube portion 114p are dissimilar.

Referring also to FIG. 1B, in some embodiments (such as the depicted embodiment), the outer diameter of distal cannula tube portion 114d is larger than the outer diameter of expandable member 120 (in its contracted configuration as shown). In addition, in some embodiments the outer diameter of distal cannula tube portion 114d is larger than the outer diameter of proximal cannula tube portion 114p. Hence, with the outer diameter of the distal cannula tube portion 114d being larger than the outer diameter of the expandable member 120, the distal cannula tube portion 114d can provide protection for the expandable member 120 during insertion into the body. That is, distal cannula tube portion 114d can absorb the stresses associated with tunneling into the body structure (e.g., bone, cartilage, other tissues, etc.), so that expandable member 120 is not subjected to such stresses. Moreover, the distal leading-end 115 of distal cannula tube portion 114d can be tapered or beveled as shown. Such a taper (along with the pointed tip of stylet 150) can help facilitate the insertion of needle-mounted balloon system 100 with less force required and less trauma induced.

In some embodiments, one or more radiopaque markers are included on one or more locations on proximal cannula tube portion 114p, mid-body cannula tube portion 114m, and/or distal cannula tube portion 114d.

Example needle-mounted balloon system 100 also includes expandable member 120. In the depicted embodiment, expandable member 120 is a balloon device affixed to cannula 110. Expandable member 120 is reconfigurable between a contracted configuration and a diametrically expanded configuration by pressurizing expandable member 120 using an inflation fluid. In some embodiments, the length of expandable member 120 (without limitation) is in a range from about 10.0 mm to about 12.0 mm, or about 11.0 mm to about 13.0 mm, or about 12.0 mm to about 14.0 mm, or about 13.0 mm to about 15.0 mm, or about 14.0 mm to about 16.0 mm, or about 15.0 mm to about 17.0 mm, or about 16.0 mm to about 18.0 mm, about 17.0 mm to about 19.0 mm, about 18.0 mm to about 20.0 mm, about 19.0 mm to about 22.0 mm, about 20.0 mm to about 24.0 mm, about 22.0 mm to about 26.0 mm, about 24.0 mm to about 30.0 mm, or greater than 30 mm, or any other suitable length.

In some embodiments, expandable member 120 is made of a material and structured to have a high burst pressure (e.g., about 20 atmospheres, about 30 atmospheres, about 40 atmospheres, or more). Expandable member 120 can be made of materials such as, but not limited to, flexible polyvinyl chloride (PVC), polyester (PET), Nylons, Pebax, polyurethane, polyurethanes blends, and the like, and combinations thereof. Expandable member 120 can be made with a single layer, dual layers, or more than two layers of material.

In some embodiments, an optional protective sleeve or shell (not shown) is included that surrounds expandable member 120 (in its contracted configuration). The sleeve can serve to protect expandable member 120 during insertion of cannula 110. Then, in some embodiments, inflation of expandable member 120 can fracture the sleeve so that expandable member 120 can inflate to its expanded configuration. Alternatively, in some embodiments the clinician-user can retract the protective sleeve prior to inflation of expandable member 120.

In some embodiments, one or more radiopaque markers are included on one or more locations on expandable member 120.

Example needle-mounted balloon system 100 also includes stylet 150. Stylet 150 includes a stylet hub 152 and a needle 154 that extends distally from stylet hub 152. In the depicted embodiment, stylet 150 is slidably disposed within cannula 110 such that hub 152 extends proximally from cannula hub 112. Stylet hub 152 can be configured for convenient manual gripping by a clinician.

A sharp distal tip portion 156 extends distally beyond the extreme distal end of cannula 110 when stylet 150 is fully engaged within cannula 110. The sharp distal tip portion 156 can be configured with various styles of tips such as, but not limited to, cone, bevel, dual gauge, and the like.

Stylet 150 serves to make the insertion of cannula 110 more safe and effective. For example, stylet 150 includes sharp distal tip portion 156, which is suitable for piercing tissues as needle-mounted balloon system 100 is being inserted. Additionally, stylet 150 provides or supplements the column strength of needle-mounted balloon system 100 so that cannula 110 can be inserted to a target area of the patient's anatomy. In some embodiments, stylet 150 is malleable so that a clinician can form stylet 150 into a curved shape if so desired.

In some embodiments, stylet 150 is made of a metallic material such as, but not limited to, stainless steel, stainless steel alloys, nitinol, titanium, titanium alloys, and the like. In some embodiments, stylet 150 is made of a polymeric material.

Figure 2:
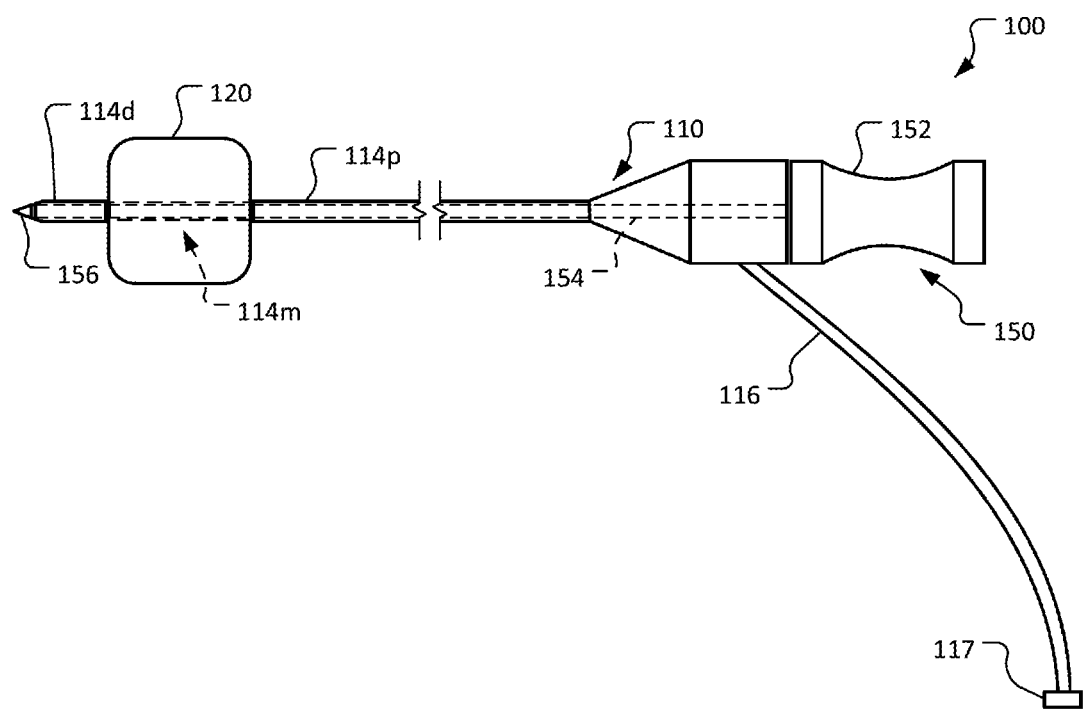
FIG. 2 is a side view of the example needle-mounted balloon system for bone expansion of FIG. 1. The needle-mounted balloon system is shown with its balloon in an expanded/inflated configuration.

Referring also FIG. 2, expandable member 120 of example needle-mounted balloon system 100 can be configured in an expanded configuration as shown in FIG. 2. In the depicted embodiment, expandable member 120 can be inflated to the diametrically symmetrical expanded configuration by pressurizing expandable member 120 using an inflation fluid as described above.

In some embodiments, the expanded outer diameter of expandable member 120 (without limitation) is in a range of about 8 mm to about 10 mm, about 9 mm to about 11 mm, about 10 mm to about 12 mm, about 11 mm to about 13 mm, about 12 mm to about 14 mm, about 13 mm to about 15 mm, about 14 mm to about 16 mm, about 15 mm to about 17 mm, about 16 mm to about 18 mm, about 17 mm to about 19 mm, about 18 mm to about 20 mm, about 19 mm to about 21 mm, or greater than 21 mm.

In some embodiments, a radiopaque solution is used as the inflation media for expandable member 120. In some embodiments, another type of fluid (e.g., saline) is used as the inflation media.

After inflating expandable member 120 to the expanded configuration, in some embodiments expandable member 120 can be deflated so that expandable member 120 returns to, or near to, the contracted configuration as shown in FIG. 1.

Referring to also FIG. 3, stylet 150 can be slidably removed from engagement with cannula 110. When stylet 150 is removed from cannula 110 (as shown in FIG. 3), connection member 118 is accessible. In some embodiments, connection member 118 is a luer or luer-lock fitting. In some embodiments, connection member 118 includes a valve, septum, or another type of fitting.

Connection member 118 is in fluid communication with the lumen of cannula 110 (i.e., the lumen previously occupied by stylet 150). Accordingly, a filler material (e.g., bone cement, or another type of flow-able material) can be injected via cannula 110 by connecting a filler material source to connection member 118 and pressurizing the filler material. In result, filler material will flow out from distal cannula tube portion 114d. In some implementations, as described further below in reference to FIG. 8, filler material that is injected via cannula 110 will fill a space that was previously created or enlarged by the expansion of expandable member 120.

Figure 4:
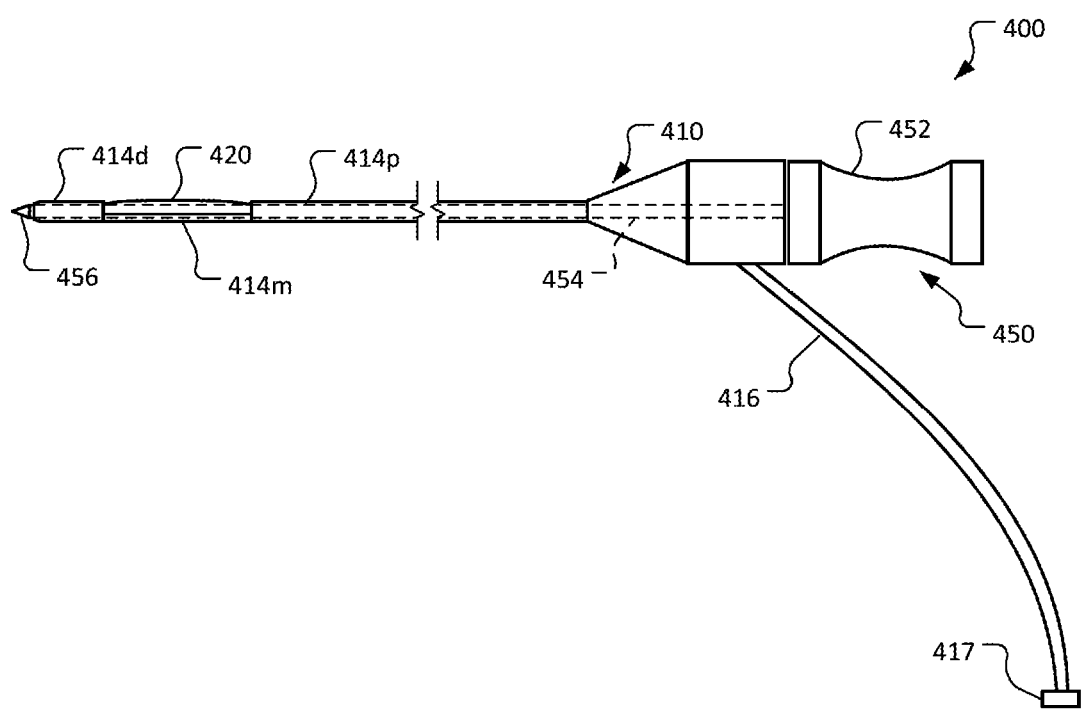
FIG. 4 is a side view of another example needle-mounted balloon system for bone expansion in accordance with some embodiments provided herein. The needle-mounted balloon system is shown with its balloon in a contracted configuration.
Figure 5:
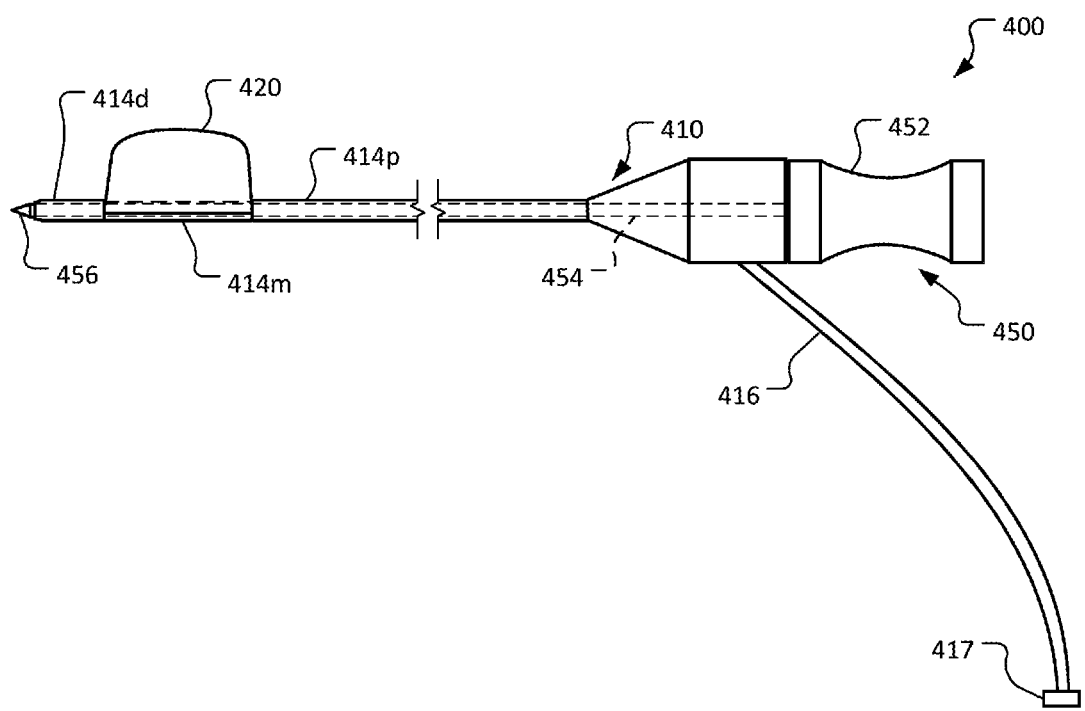
FIG. 5 is a side view of the example needle-mounted balloon system for bone expansion of FIG. 5. The needle-mounted balloon system is shown with its balloon in an expanded configuration.

Referring to FIGS. 4 and 5, an example needle-mounted balloon system 400 is configured like needle-mounted balloon system 100, except that needle-mounted balloon system 400 includes a diametrically asymmetrical expandable member 420. Asymmetrical expandable member 420 is shown in its contracted configuration in FIG. 4 and in its expanded configuration in FIG. 5

It should be understood that the expandable members of the needle-mounted balloon system provided herein can be selected to have any desirable shape, size, configuration, material, and other properties.

In some embodiments, the needle-mounted balloon systems provided herein can include two or more expandable members that may be either independently or collectively inflatable. In some such embodiments, one or more of the expandable members can be configured to provide a seal to contain injected filler material within the space being filled. In one such example, a cannula of a needle-mounted balloon system includes two balloons that are individually inflatable and deflatable. The two balloons can be arranged generally adjacent to each other, with a first balloon being a distal balloon and a second balloon being a proximal balloon (located proximally of the first balloon). After inserting the balloons into the target body structure, both balloons can be inflated. Then, the distal balloon can be deflated while the proximal balloon remains inflated. Then, the filler material can be injected to fill the space previously occupied by the expanded distal balloon. While the filler material is filling the space, the inflated proximal balloon acts as a seal or a dam to help ensure that the filler material is contained only in the space previously occupied by the expanded distal balloon.

Figure 6:
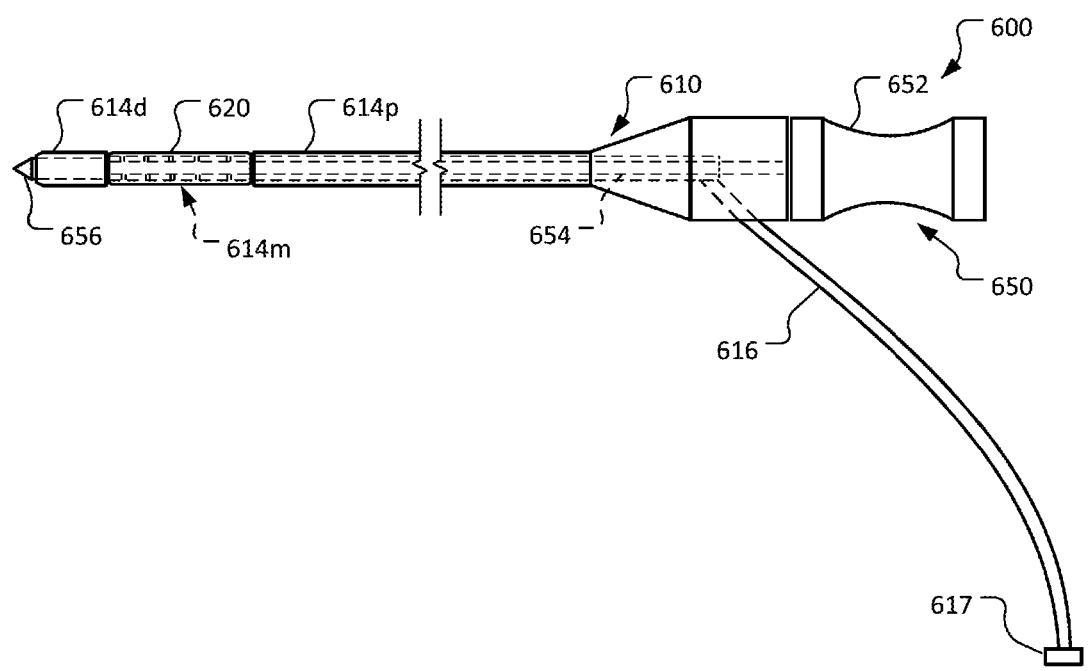
FIG. 6 is a side view of another example needle-mounted balloon system for bone expansion in accordance with some embodiments provided herein. The needle-mounted balloon system is shown with its balloon in a contracted configuration.
Figure 7:
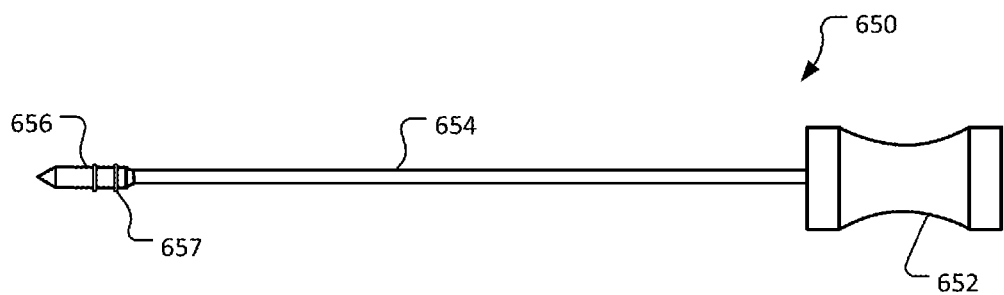
FIG. 7 is a side view of a stylet that can be used with the needle-mounted balloon system of FIG. 6

Referring to FIGS. 6 and 7, an example needle-mounted balloon system 600 can include a stylet 650 with a mid-body portion 654 that is configured to provide a space for an inflation fluid to flow within the lumen of cannula 610 from cannula hub 612 to expandable member 620. A distal end portion 656 of stylet 650 can be larger such that distal end portion 656 slidably seals with the lumen of cannula 610. Accordingly, when a source of inflation fluid (e.g., saline) is coupled with inflation tube 616 (e.g., via a connection 617), expandable member 620 can be inflated or deflated by pressurizing or depressurizing the source of inflation fluid.

Mid-body portion 654 defines a one or more openings that allow passage of the inflation fluid between the lumen of cannula 610 and the interior of expandable member 620. In this configuration, the expandable member 620 is only expandable when the stylet 650 is engaged with the cannula 610.

In some embodiments, one or more compliant sealing members 657 (e.g., O-rings) are disposed between the inner diameter of the distal cannula tube portion 614d and the outer diameter of the distal end portion 656 of stylet 650. Such compliant sealing member(s) 657 can help ensure that the pressurized inflation fluid is directed solely into expandable member 620 and can help maintain the pressure of the inflation fluid in expandable member 620 while expandable member 620 is inflated.

The configuration of example needle-mounted balloon system 600 eliminates the need for an inflation lumen between cannula hub 612 and expandable member 620, thereby simplifying the overall design. Therefore, needle-mounted balloon system 600 may be particularly cost effective to manufacture and/or convenient to operate.

Figure 8:
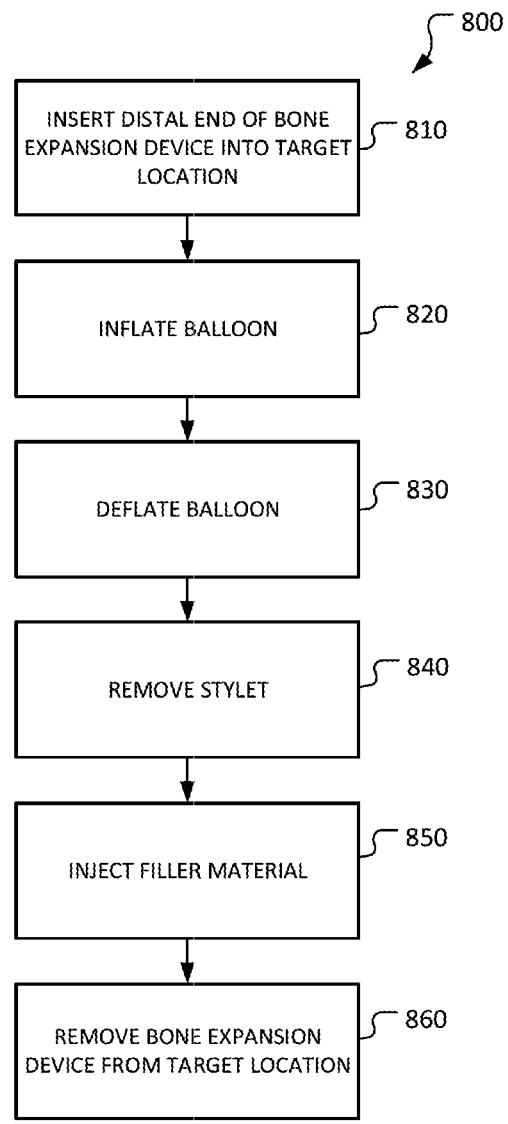
FIG. 8 is a flowchart of a method for creating a space in a body and injecting a filler material into the space, using the needle-mounted balloon systems for bone expansion provided herein, in accordance with some embodiments.

Referring to FIG. 8, a method 800 for creating a space and injecting a filler material (e.g., a cementoplasty method), using the needle-mounted balloon systems for bone expansion provided herein, is depicted in a flowchart.

At step 810, at least a distal end portion of a needle-mounted balloon system (e.g., as described above) is inserted to a target location. In some embodiments, this step is performed using fluoroscopy or another type of imaging modality. Optionally, after completion of step 810, the stylet of the needle-mounted balloon system can be removed from the cannula of the needle-mounted balloon system.

At step 820, a balloon device of the needle-mounted balloon system is inflated to expand the diameter of the balloon device. For example, a source of inflation fluid can be connected to the needle-mounted balloon system and activated to pressurize the balloon device. In result, the expanded balloon device may create a space at the target location as desired. Optionally, after completion of step 820, the stylet of the needle-mounted balloon system can be removed from the cannula of the needle-mounted balloon system.

At step 830, the balloon device of the needle-mounted balloon system is deflated to contract the diameter of the balloon device. For example, the source of inflation fluid can be activated to depressurize the balloon device. In result, when the balloon device has been deflated, the space previously occupied by the balloon device at the target location may at least partially remain.

At step 840, the stylet of the needle-mounted balloon system is removed from the cannula of the needle-mounted balloon system (unless it was previously removed). The resulting configuration of the cannula is shown, for example, in FIG. 3. It should be understood that for example needle-mounted balloon system 600, the stylet cannot be removed until step 840. However, for the other embodiments of needle-mounted balloon systems, the stylet can optionally be removed any time after the completion of step 810 and prior to step 850.

At step 850, filler material (e.g., bone cement or other flow-able material) is injected to the space via the cannula of the needle-mounted balloon system. For example, as described above in reference to FIG. 3, a source of filler material can be connected to a connection member of the cannula, and the filler material can be pressurized to make it flow out from a distal portion of the cannula and into the space. The space may be partially or substantially completely filled by the filler material.

At step 860, the needle-mounted balloon system is retracted from the target location. In some embodiments, process 800 may be repeated in another location that is near to, or adjacent to, the target location. When the needle-mounted balloon system has been retracted, the filler material remains within the space at the target location. For example, in some implementations bone cement remains within the space created by the expanded balloon device within the bone structure.

Figure 9:
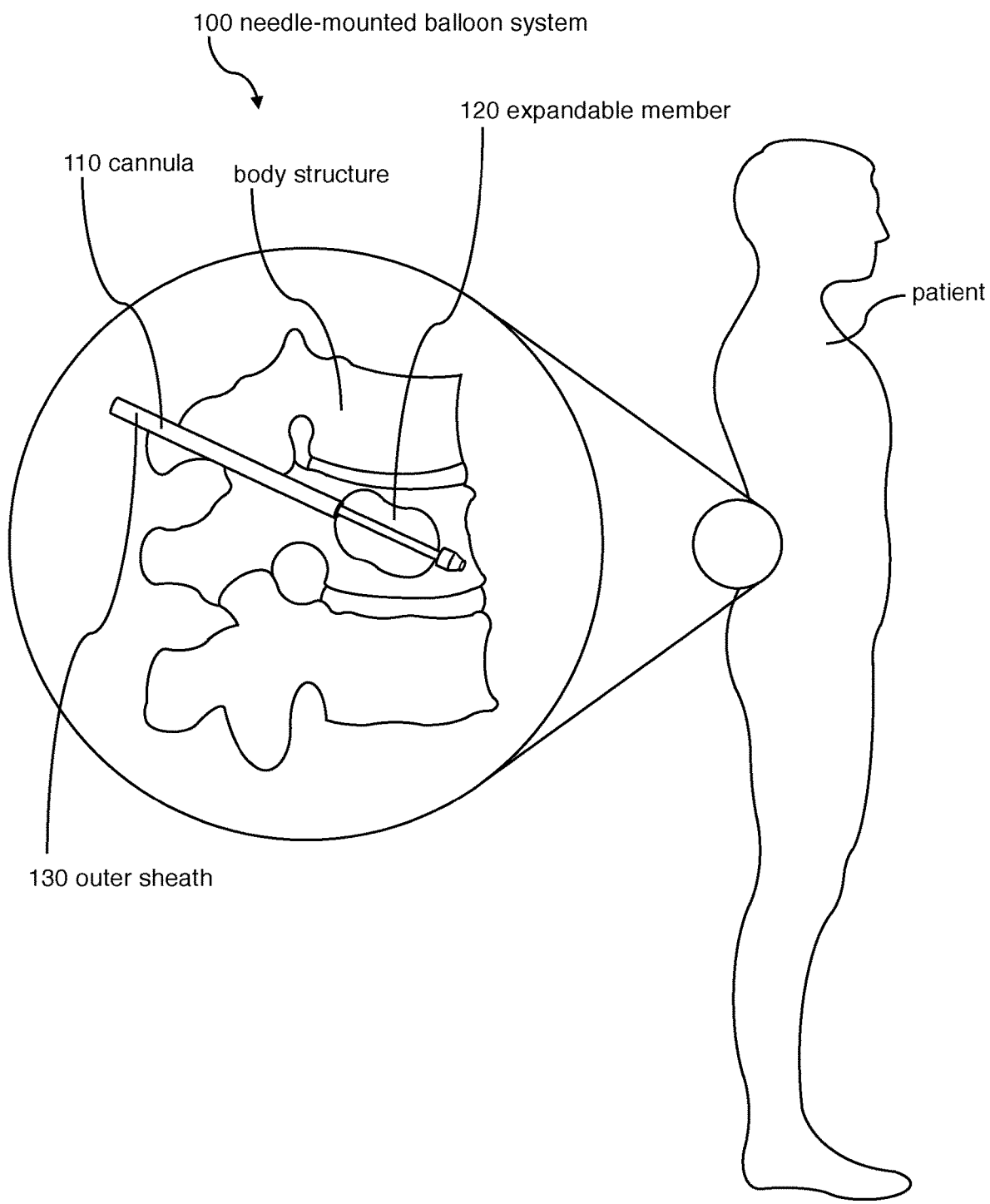
FIG. 9 illustrates a perspective view of a needle-mounted balloon system inserted into a body structure, according to some embodiments.

Referring now to FIG. 9, a perspective view of a needle-mounted balloon system 100 is shown in the body structure of a patient. In the embodiment shown in FIG. 9, the body structure is located in the patient's spinal column. The system 100 is depicted with the cannula 110 inserted, the outer sheath 130 retracted, and the expandable member 120 inflated within a bone of the spinal column. Each of these elements will be discussed in further detail throughout this disclosure.

Figure 10:
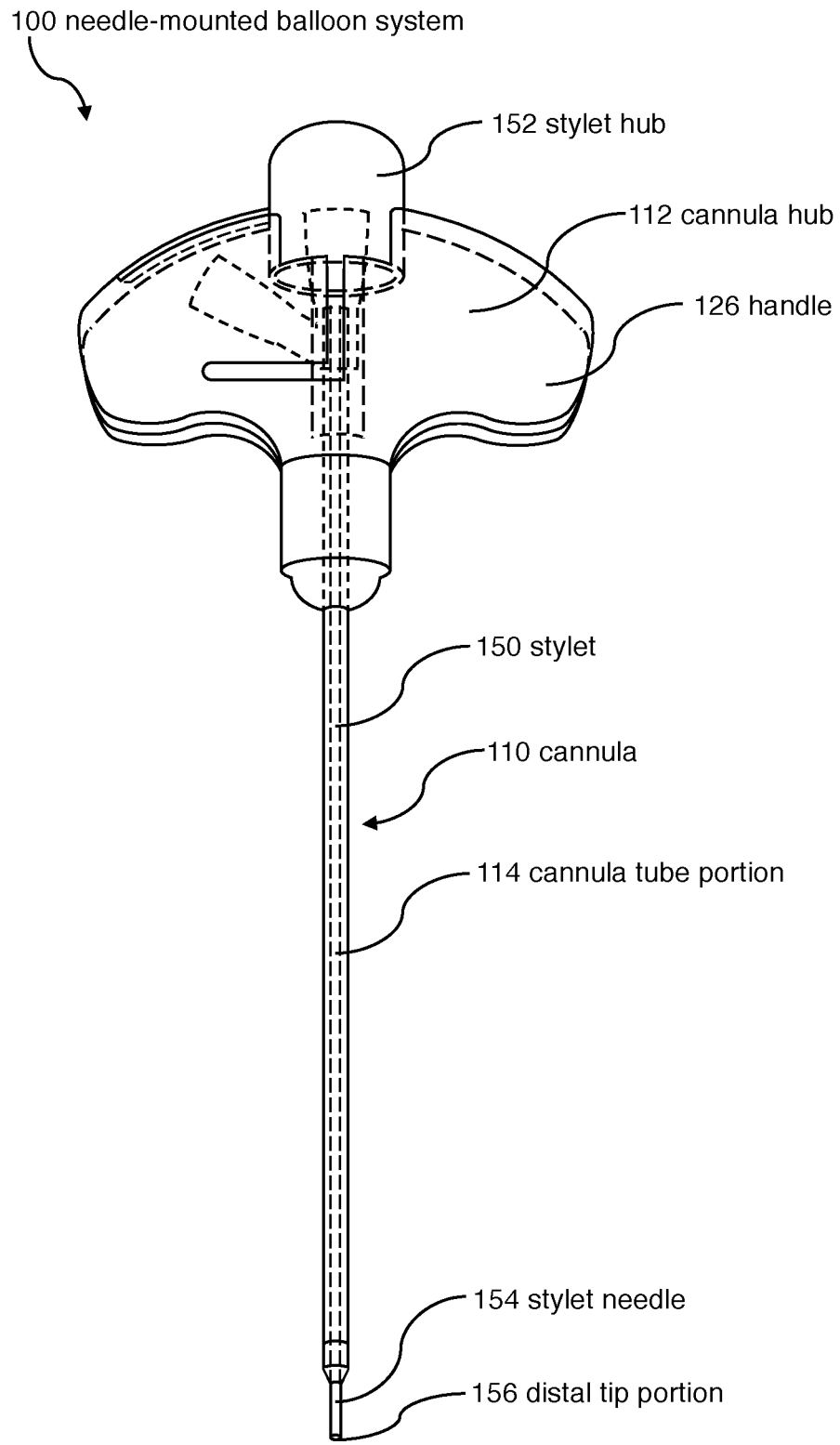
FIG. 10 illustrates a perspective view of a needle-mounted balloon system, according to some embodiments.
Figure 11A:
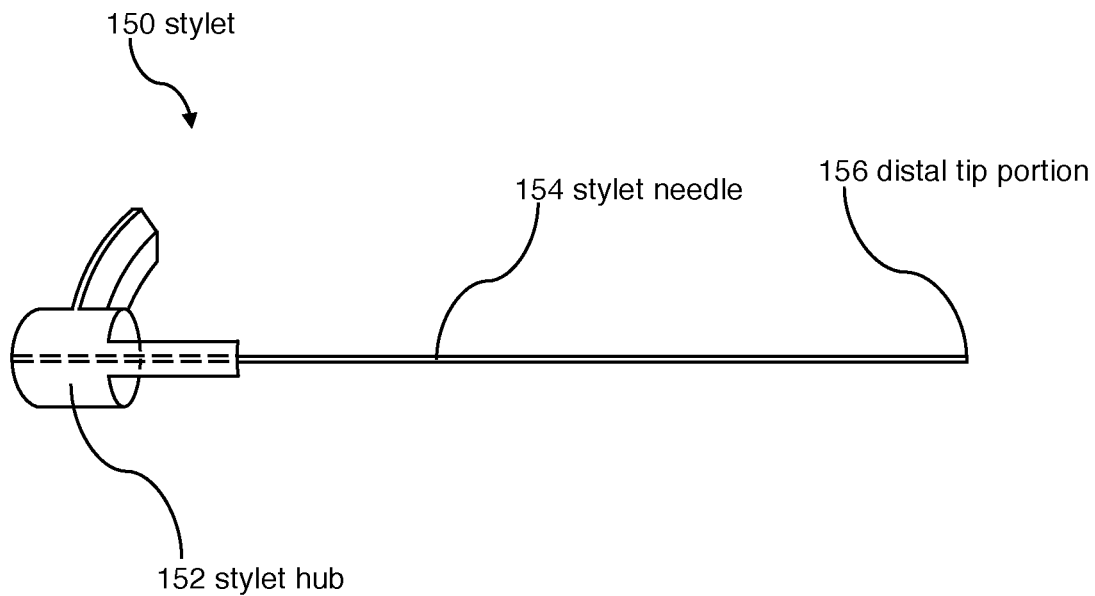
FIGS. 11A and 11B illustrate perspective views of a dismantled needle-mounted balloon system, according to some embodiments.
Figure 12A:
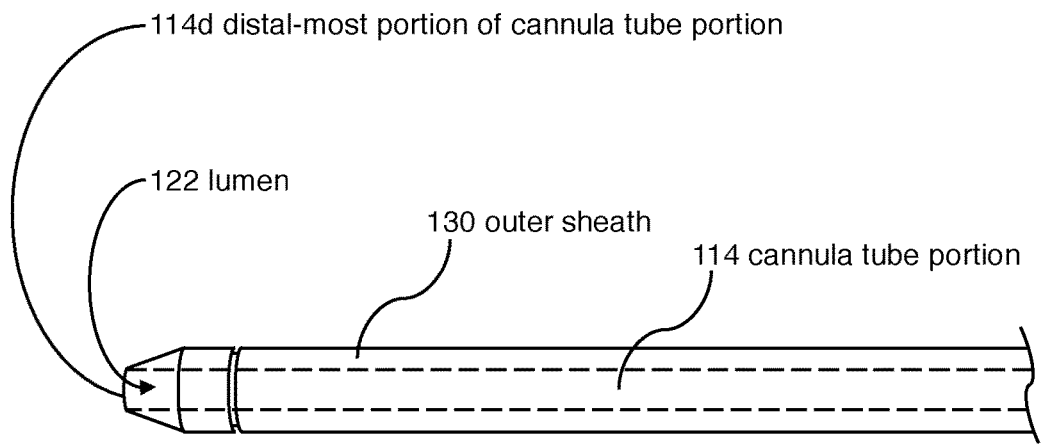
FIGS. 12A and 12B illustrate perspective views of a distal portion of a needle-mounted balloon system, according to some embodiments.
Figure 12B:
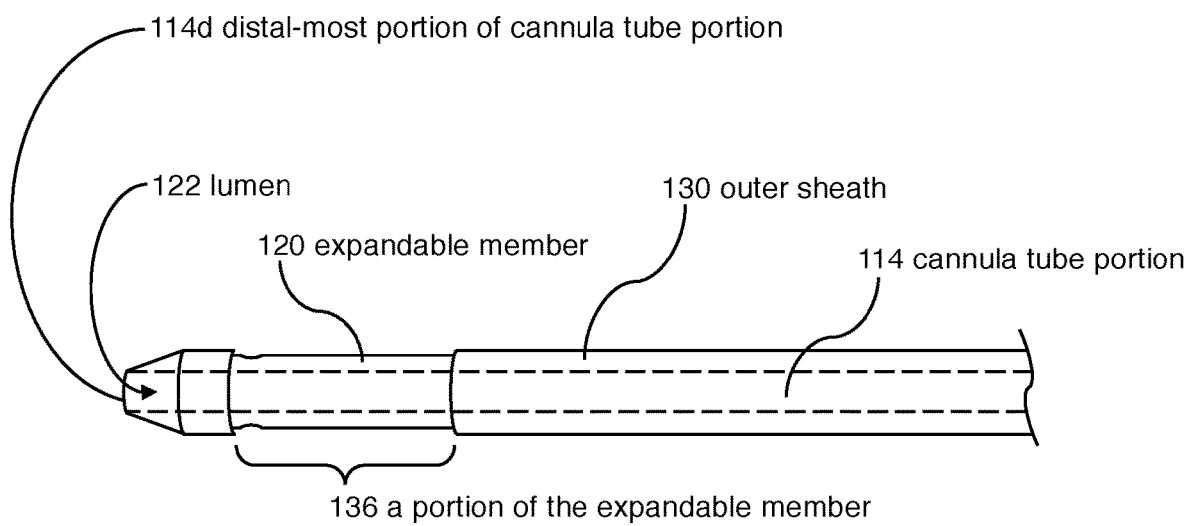

FIG. 10 illustrates an example of a needle-mounted balloon system 100. The system 100 may include a cannula 110 and a stylet 150, which is shown in FIG. 11A. In some embodiments, the cannula 110 includes a cannula hub 112 and a cannula tube portion 114 extending distally from the cannula hub 112. The cannula tube portion 114 may be hollow such that the cannula tube portion 114 defines a lumen 122 therethrough (lumen 122 is shown in FIGS. 12a and 12b).

Figure 11B:
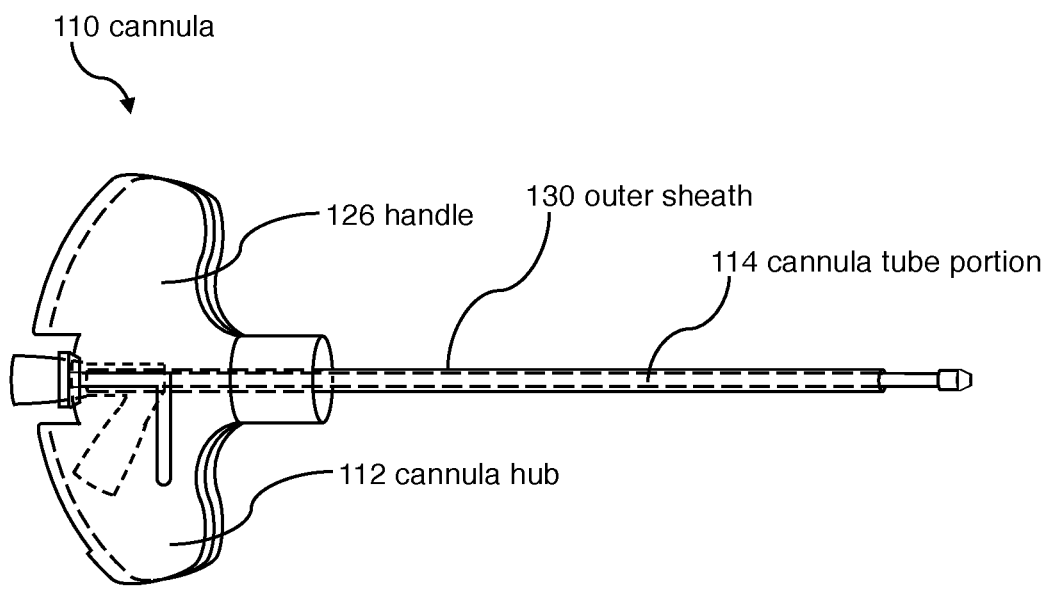

FIGS. 11A and 11B show the needle-mounted balloon system 100 with the stylet 150 removed from the cannula 110, according to some embodiments. As illustrated by FIG. 11A, the stylet 150 may include a stylet hub 152, a stylet needle 154, and a distal tip portion 156. The stylet needle 154 may extend distally from the stylet hub 152. The distal tip portion 156 may be configured with various styles of tips, including, but not limited to, cone, bevel, dual gauge, and the like. In some embodiments, the stylet needle 154 is hollow. Alternatively, in some embodiments, the stylet needle 154 is solid.

Figure 17A:
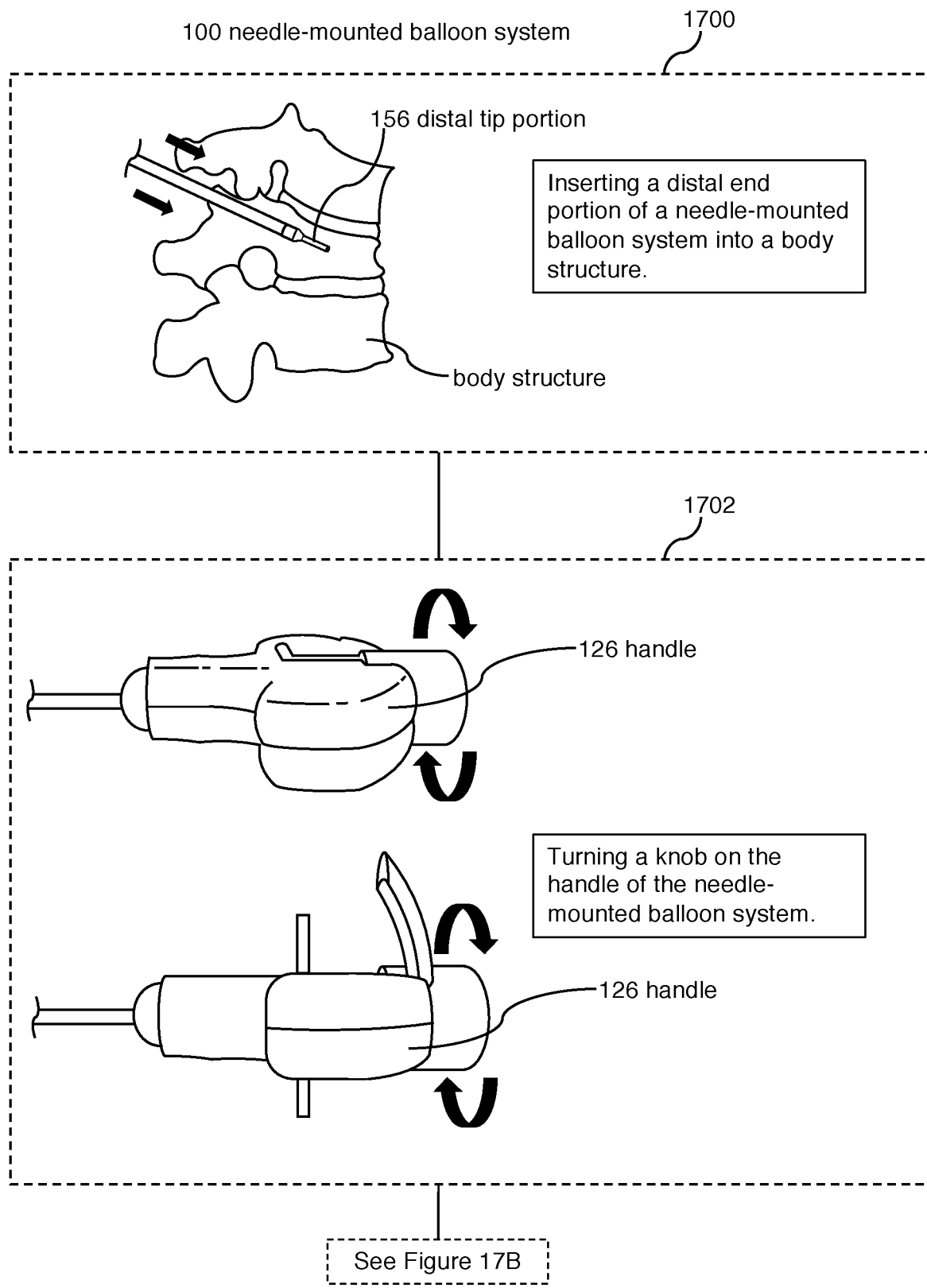
FIGS. 17A-17D illustrate a method of using a needle-mounted balloon system, according to some embodiments.

The cannula 110 may include a handle 126, the cannula hub 112, an outer sheath 130, and the cannula tube portion 114. Stated differently, the cannula hub 112 and the stylet hub 152 may both be part of a handle 126 of the system 100. In some embodiments, the stylet hub 152 is a knob configured to rotate and separate from the rest of the handle 126. This aspect of the stylet hub 152 will be discussed further with reference to FIG. 17A. The handle 126 may be included in the system 100 for convenient manual gripping by a practitioner during a procedure, as well as to provide a surface for force exertion to advance the system 100 through the body of a patient, which will also be discussed further with reference to FIG. 17A.

In some embodiments, the stylet 150 is detachably coupled with the cannula 110 such that the stylet 150 can be completely removed from the cannula 110. As shown in FIG. 10, when the stylet 150 is engaged with the cannula 110, the stylet needle 154 thereby extends through the lumen 122 within the cannula tube portion 114 such that the distal tip portion 156 extends beyond the distal-most portion 114d (see FIG. 15) of the cannula tube portion 114. This extension may serve to make the insertion of the system 100 more safe and effective. For example, the distal tip portion 156 may be sharp and suitable for piercing tissues as the needle-mounted balloon system 100 is being inserted. Additionally, the stylet needle 154 may provide or supplement the column strength of the system 100 so that the cannula 110 can be inserted to a target area of the patient's anatomy. In some embodiments, the stylet 150 is malleable so that a practitioner can form the stylet 150 into a curved shape if so desired.

Visible in FIG. 11B is a port coupled to the handle 126 of the system 100. The port is revealed upon removal of the stylet 150, and will be discussed below with reference to FIG. 13. Various components of the cannula 110 and stylet 150, including the stylet needle 154, outer sheath 130, and cannula tube portion 114 may be composed of metal materials (e.g., stainless steel, nitinol, etc.). Alternatively, these components, and/or others, may be composed of other suitable biocompatible materials.

FIGS. 12A and 12B illustrate close-up views of a distal portion of the cannula tube portion 114, according to some embodiments. The system 100 may include an outer sheath 130 configured to retract (i.e. move away from the distal-most portion of cannula tube portion 114d), as shown in FIG. 12B, to expose an expandable member 120. In some embodiments, only a portion 136 of the expandable member 120 is exposed upon retraction of the outer sheath 130. The outer sheath 130 may be slideably coupled to the cannula tube portion 114 such that the outer sheath 130 is able to slide along the outer surface of the cannula tube portion 114 to reveal the expandable member 120. Such a configuration of the system 100 may provide greater protection to the expandable member 120, as it is held between the cannula tube portion 114 and the outer sheath 130 until the outer sheath 130 is retracted. During a cementoplasty procedure, such embodiments may thereby provide a lower risk of the expandable member 120 snagging or tearing during the movement of the system 100 to the treatment location. Exact timing of the retraction of the outer sheath 130 and exposure of the expandable member 120 during a cementoplasty procedure will be discussed further with reference to FIG. 17B.

The outer sheath 130 may define a variety of gauges (or diameters). In some embodiments, the outer sheath 130 is a 10UT hypotube, which means the outer sheath 130 has a 10 gauge ultra-thin wall, having an outer diameter of about 0.134" (+/−0.001") and an inner diameter of about 0.122" (+/−0.002"). It should be appreciated that the disclosure includes many embodiments defining different dimensions of the outer sheath 130, such as 10RW (10 gauge regular wall, 0.134" outer diameter, 0.106" inner diameter), 10TW (10 gauge thin wall, 0.134" outer diameter, 0.114" inner diameter), 10XT (10 gauge extra thin, 0.134" outer diameter, 0.118" inner diameter), and the like. In some embodiments, the outer sheath 130 defines any size hypodermic stainless steel tube sold by Teshima Technology, having an office located at 1 Broadway 14F in Cambridge, Mass. Even still, in some embodiments, the outer sheath 130 defines a custom size sheath, having any size outer diameter and inner diameter. For example, the outer sheath 130 may comprise Ecamole having an outer diameter of about 0.134" and an inner diameter of about 0.124".

As will be discussed with reference to FIG. 15, the outer diameter 138 of a distal-most portion 114d of the cannula tube portion 114 is also about 0.134". This common outer diameter may ensure a smooth transition along the cannula 110 from the distal-most portion 114d of the cannula tube portion 114 to the outer sheath 130, and thereby reduce the chance of the system 100 snagging on a body structure, as may happen with substantially different outer diameters between the two components. The outer sheath 130 may comprise welded metal (e.g., stainless steel, nitinol, etc.) such that it appears seamless. Alternatively, any other suitable biocompatible material may be used to make the outer sheath 130. In some embodiments, the cannula tube portion 114 comprises an outer polymer jacket. The outer polymer jacket may be a Pellethane 75D jacket measuring 0.099" by 0.111". In some embodiments, the outer polymer jacket is pre-ablated prior to bonding the expandable member 120 to the cannula tube portion 114. Further discussion of the expandable member 120 and its coupling to the cannula tube portion 114 will be included below.

Figure 13:
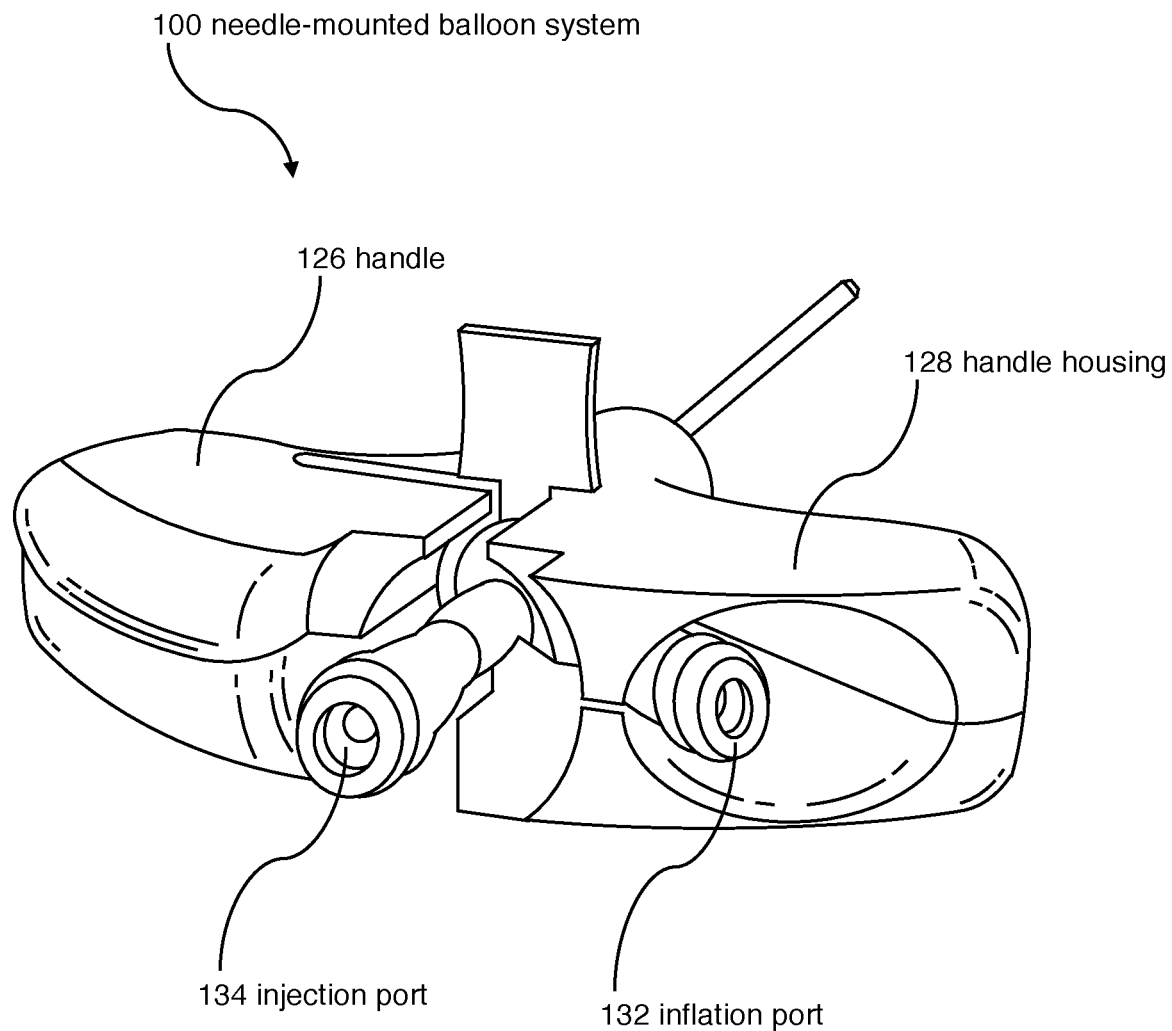
FIG. 13 illustrates a perspective view of a handle of a needle-mounted balloon system, according to some embodiments.

Referring now to FIG. 13, a close-up illustration of the handle 126 of the system 100 is shown. In some embodiments, the handle 126 includes a handle housing 128 and two ports at least partially located within the handle housing 128. In some embodiments, the two ports comprise an inflation port 132 and an injection port 134. In some embodiments, the inflation port 132 is located at an angle to the cannula tube portion 114 and is in fluid communication with the expandable member 120, while the injection port 134 is coupled to the cannula tube portion 114 such that the injection port 134 is in fluid communication with the lumen 122 of the cannula tube portion 114. As will be discussed with reference to FIGS. 9C and 9D, in some embodiments the inflation port 132 is used to inflate the expandable member 120 and the injection port 134 is used to inject filler material through the cannula tube portion 114 into a treatment location within a body structure. In many embodiments, the inflation port 132 and injection port 134 are composed of a biocompatible polymer material. The ports 40, 42 may also include a threaded outer and/or inner surface to facilitate coupling of a pressurizing device, such as a syringe, for use in inflation of the expandable member 120 and/or injection of the filler material.

Figure 14A:
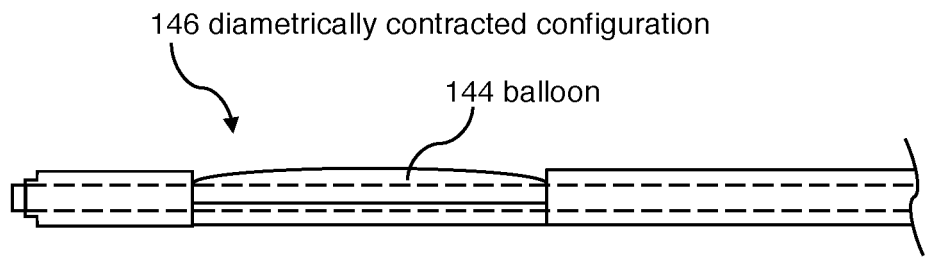
FIGS. 14A-14C illustrate perspective views of a balloon of a needle-mounted balloon system, according to some embodiments.
Figure 14B:
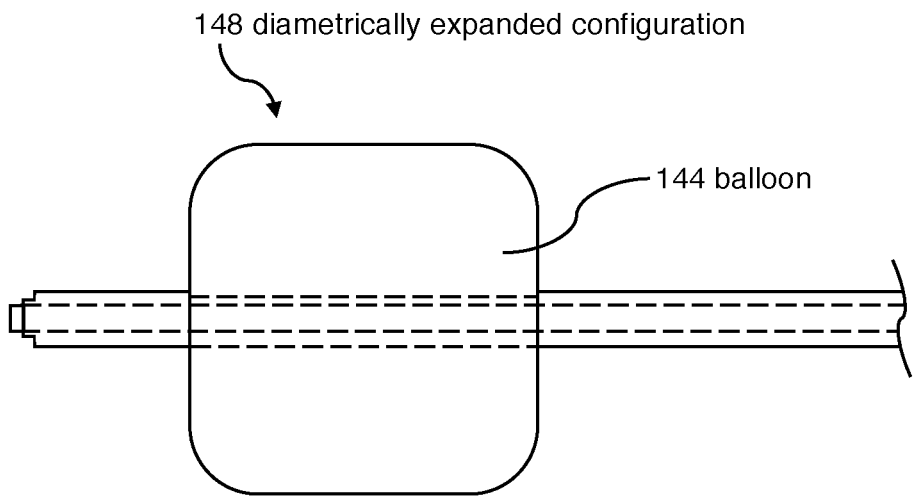
Figure 14C:
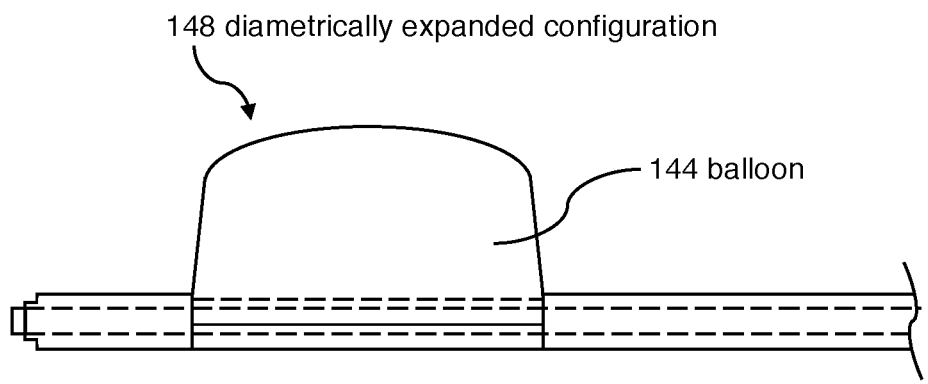

FIGS. 14A-14C illustrate a balloon 144 according to different embodiments. It should be noted that, in many embodiments, the expandable member 120 discussed throughout this disclosure is a balloon 144, as such the terms balloon 144 and expandable member 120 may be used interchangeably throughout this disclosure. In the diametrically expanded configuration 148, a balloon 144 may be diametrically symmetrical, as illustrated by FIG. 14B. Alternatively, a balloon 144 in the diametrically expanded configuration 148 may be diametrically asymmetrical, as illustrated by FIG. 14C. FIG. 14A shows the balloon 144 in the diametrically contracted configuration 146. In many embodiments, the balloon 144 is in the diametrically contracted configuration 146 prior to retraction of the outer sheath 130 and inflation of the balloon 144.

In some embodiments, the balloon 144 is a dual-layer balloon. In such embodiments, each layer of the balloon may comprise a 90AE balloon with a thickness of about 0.012". In some embodiments, each balloon that makes up the dual-layer balloon 144 may have a different thickness. The outer balloon may be a thinner balloon than the inner balloon. Alternatively, the outer balloon may be a thicker balloon than the inner balloon. The use of a dual-layer balloon, as opposed to the traditional single-layer balloon, may provide greater strength and resiliency to the balloon 144 and prevent bursting of the balloon 144 during a procedure. The bursting of a balloon during a procedure such as cementoplasty can be very detrimental and cause delays in the procedure time, particularly if the balloon bursts before an adequate space is created in a bone structure. A stronger balloon, such as the dual-layer balloon included in this disclosure, may facilitate quicker and more effective cementoplasty procedures with fewer issues and delays.

The balloon 144 may be comprised of materials such as, but not limited to, flexible polyvinyl chloride (PVC), polyester (PET), Nylons, Pebax, polyurethane, polyurethane blends, etc., and combinations thereof. In some embodiments, the dual layers of the balloon 144 are coupled together via heat bonding. Prior to heat bonding, the inner balloon and/or both balloons may be adhered to the outer surface of the cannula tube portion 114. The balloon(s) may be adhered using Epoxy, or any other suitable biocompatible adhesive. Adherence and bonding of the dual-layer balloon 144 may occur in various ways. In one embodiment, the inner balloon may be folded around the cannula tube portion 114, and then the outer balloon may be loaded over the inner balloon to create the dual-layer balloon. Alternatively, the outer balloon may be loaded over the inner balloon prior to folding around, and adherence to, the cannula tube portion 114. In some embodiments, the balloon 144 may be made of more or fewer than two layers. It should be understood that the balloon 144 of the system 100 provided herein can be selected to have any desirable shape, size, configuration, material, and/or other properties.

Figure 15:
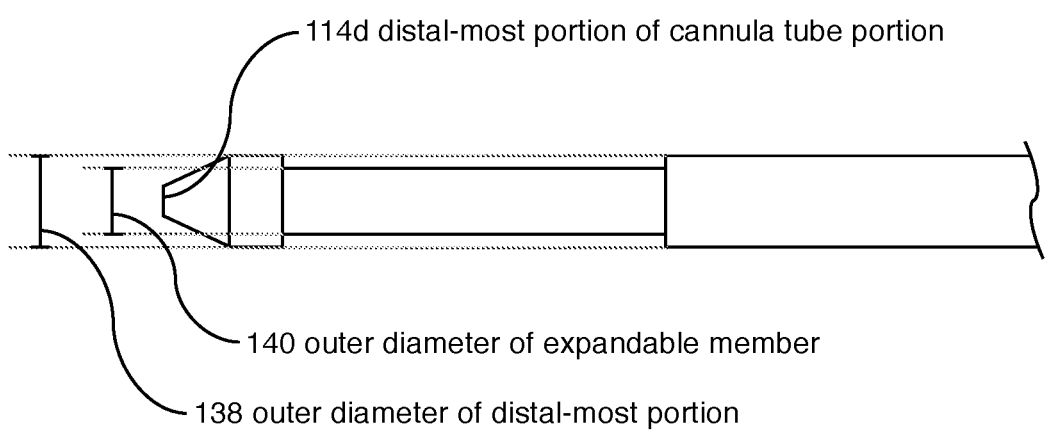
FIG. 15 illustrates a perspective view of a distal portion of a needle-mounted balloon system, according to some embodiments.

Referring now to FIG. 15, in some embodiments, the outer diameter 140 of the expandable member 120 is less than the outer diameter 138 of the distal-most portion 114d of the cannula tube portion 114. In many embodiments, this difference is applicable when the expandable member 120 is in the diametrically contracted configuration 146. When the expandable member 120 is in the diametrically expanded configuration 148, the outer diameter 140 of the expandable member 120 may be greater than the outer diameter 138 of the distal-most portion 114d of the cannula tube portion 114. In some embodiments, the outer diameter 138 of the distal-most portion 114d of the cannula tube portion 114 is about 0.134". The outer diameter 140 of the expandable member 120 may be about 0.120" in the diametrically contracted configuration 146. The cannula tube portion 114, with the exception of the distal-most portion 114d, may measure about 0.070" by 0.095".

Figure 16:
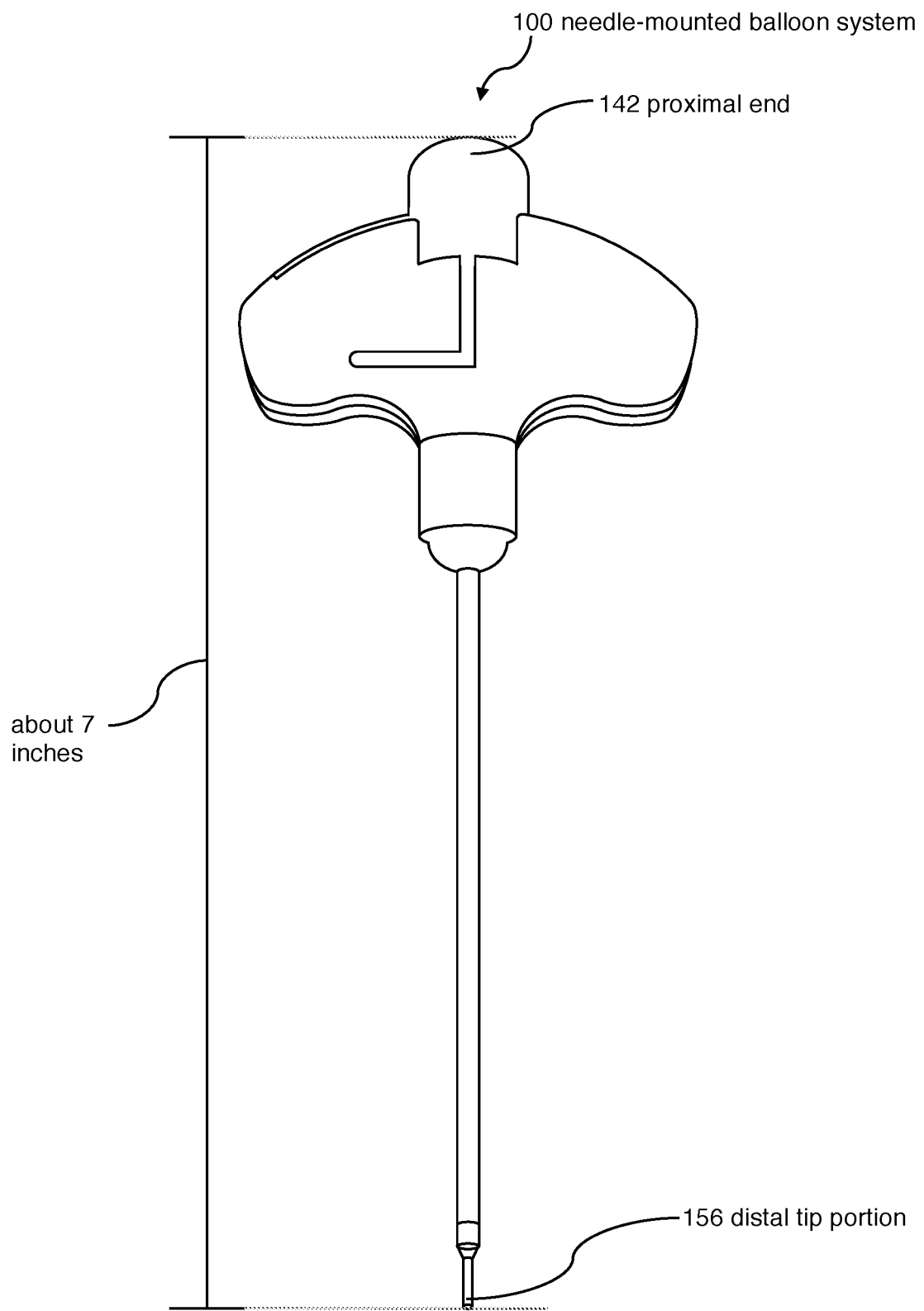
FIG. 16 illustrates a perspective view of a needle-mounted balloon system, according to some embodiments.

FIG. 16 illustrates a perspective view of a needle-mounted balloon system 100 and illustrates that, in some embodiments, the total length of the system 100 from the distal tip portion 156 to a proximal end 142 of the handle 126 is about 7". In some embodiments, the total length of the system 100 is greater than 7". Alternatively, the total length of the system 100 may be less than 7". Upon removal of the stylet 150, the length of the system 100 decreases by about 0.24", as the distal tip portion 156 of the stylet needle 154 extends beyond the distal-most portion 114d of the cannula tube portion 114 a distance of about 0.24".

FIGS. 17A-17D illustrate diagrammatic views of a cementoplasty procedure performed with a needle-mounted balloon system 100, according to some embodiments. Beginning with FIG. 17A, at step 1700, at least the distal end of the needle-mounted balloon system 100 is inserted into a body structure. In some embodiments, this step is performed using fluoroscopy or another type of imaging modality. In many embodiments, the body structure is bone. In some embodiments, the body structure is a weakened portion of the spinal column. The system 100 may be inserted into the body structure with the help of a force exerted on the handle 126. For example, a practitioner may use a hammer to tap the knob on the handle 126 and advance the system 100 through the body. The stylet needle 154 may also play a key role in insertion of the system 100, as the stylet needle 154 is a focused point to carve a path through the body to the target body structure.

Following insertion of the distal end, a practitioner may turn a knob on the handle 126 of the system 100. As was discussed previously in this disclosure, the knob may be the same component as the stylet hub 152. As shown in step 1702, turning the knob may reveal two plastic tabs protruding from opposite faces of the handle 126, as well as an additional tab that is part of the knob. In many embodiments, turning the knob comprises a quarter turn. In some embodiments, the tabs are not revealed until the knob is turned in order to simplify the system 100 and help practitioners proceed in the most effective order. For example, the outer sheath 130 may be configured to not be able to be retracted until the stylet needle 154 is disengaged from the cannula 110, so the mechanisms to retract the outer sheath 130 (the tabs) do not need to be revealed until the stylet 150 is removed and/or in the process of being removed.

Figure 17B:
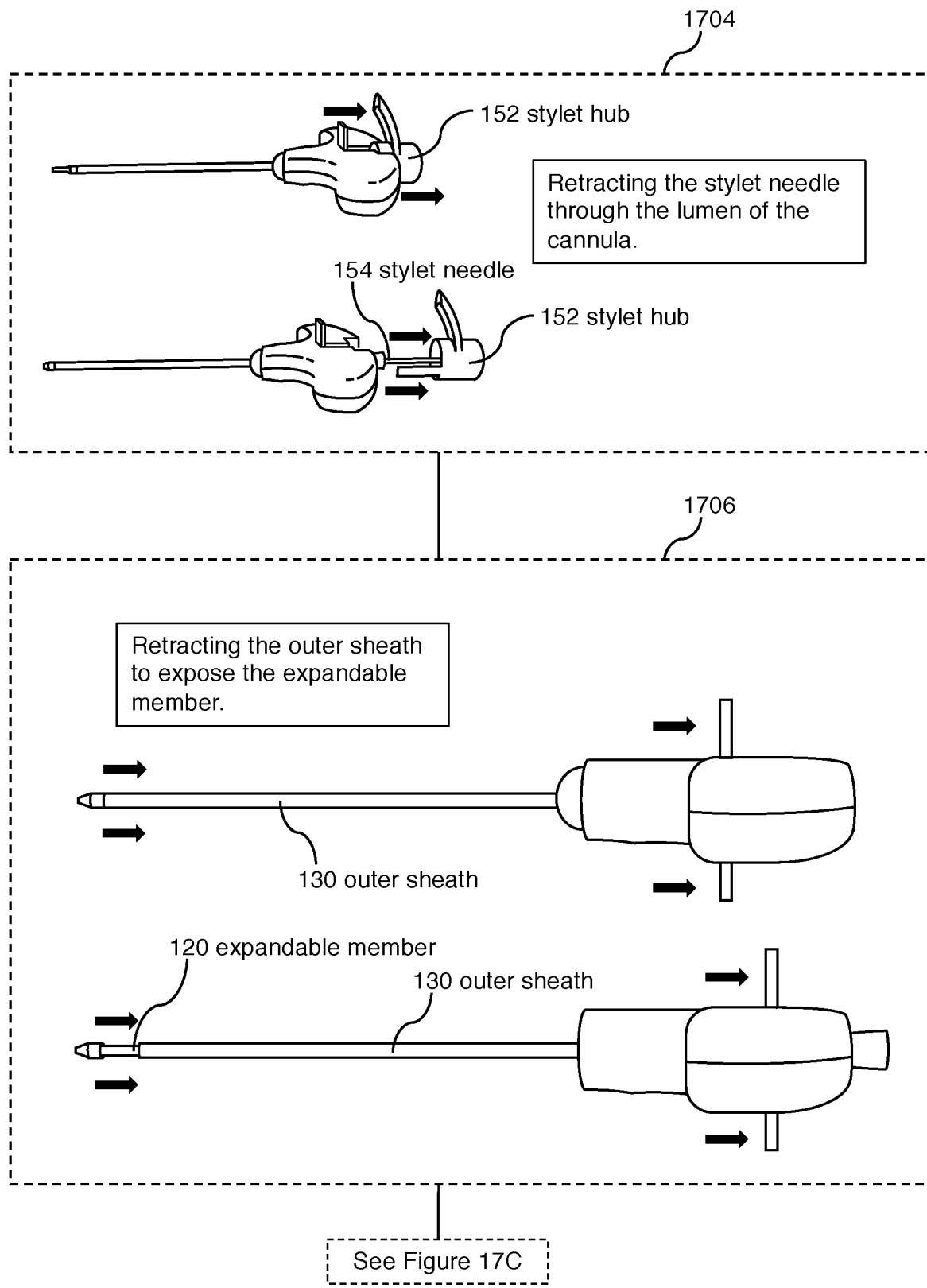

Referring now to FIG. 17B, step 1704 illustrates retraction of the stylet needle 154 through the lumen 122 of the cannula 110. A practitioner may pull the knob (stylet hub 152) in a proximal direction in order to retract the stylet needle 154 through the lumen 122 of the cannula tube portion 114. In many embodiments, the stylet 150 must completely disengage from the cannula 110 in order for the procedure to continue. Following retraction of the stylet 150, the system 100 may resemble FIGS. 11A and 11B, where the stylet 150 is shown completely disengaged from the cannula 110. Next, a practitioner may pull the two protruding tabs in a proximal direction, as shown in step 1706, in order to retract the outer sheath 130 and at least partially expose the expandable member 120. In some embodiments, turning the knob at step 1702 may reveal more or fewer than two tabs coupled to the handle 126. In such an embodiment(s), the practitioner may pull the more or fewer than two tabs in a proximal direction in order to retract the outer sheath 130. It should be noted, the illustration for step 1706 intentionally omits the body structure of the patient so that the figure can clearly illustrate retracting the outer sheath 130.

Figure 17C:
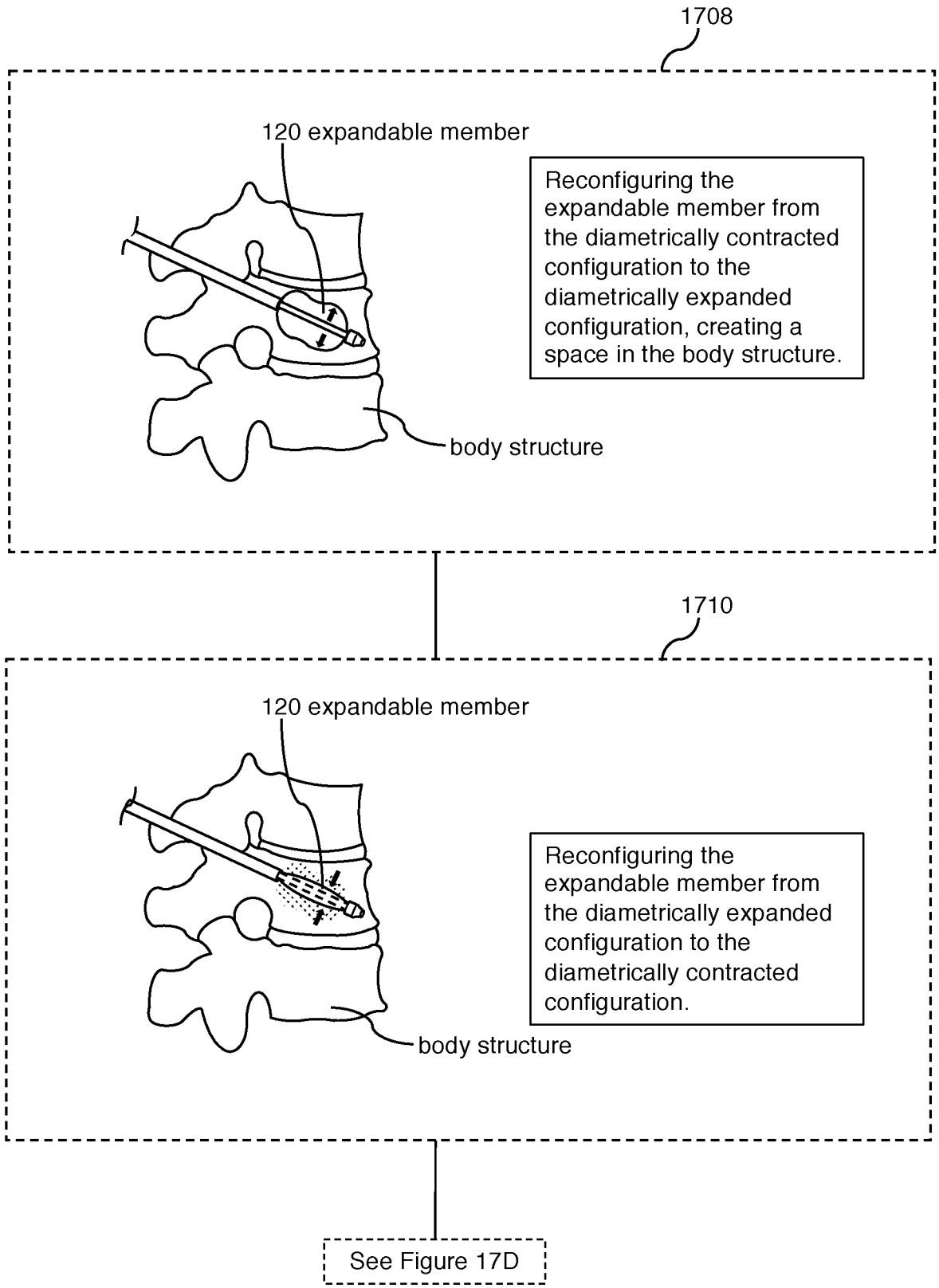

FIG. 17C illustrates the steps of reconfiguring the expandable member 120 from the diametrically contracted configuration 146 to the diametrically expanded configuration 148, at step 1708 (hereafter referred to as "inflating the balloon 144"), and then reconfiguring the expandable member 120 from the diametrically expanded configuration 148 to the diametrically contracted configuration 146, at step 1710 (hereafter referred to as "deflating the balloon 144"). In many embodiments, the balloon 144 is inflated to create an open space within the body structure, and then deflated to make room for the filler material. The balloon 144 may be inflated by injecting an inflation fluid through the inflation port 132 shown in detail in FIG. 13. In some embodiments, the inflation fluid is comprised of saline, contrast dye, or a combination. Alternatively, the inflation fluid may be any other suitable biocompatible material or combination of suitable biocompatible materials. Contrast dye may be used as an aid in visualization of the body structure and the system 100, particularly in procedures carried out with image guidance. The balloon 144 may be inflated and deflated by pressurizing and depressurizing, respectively, the source of the inflation fluid.

Figure 17D:
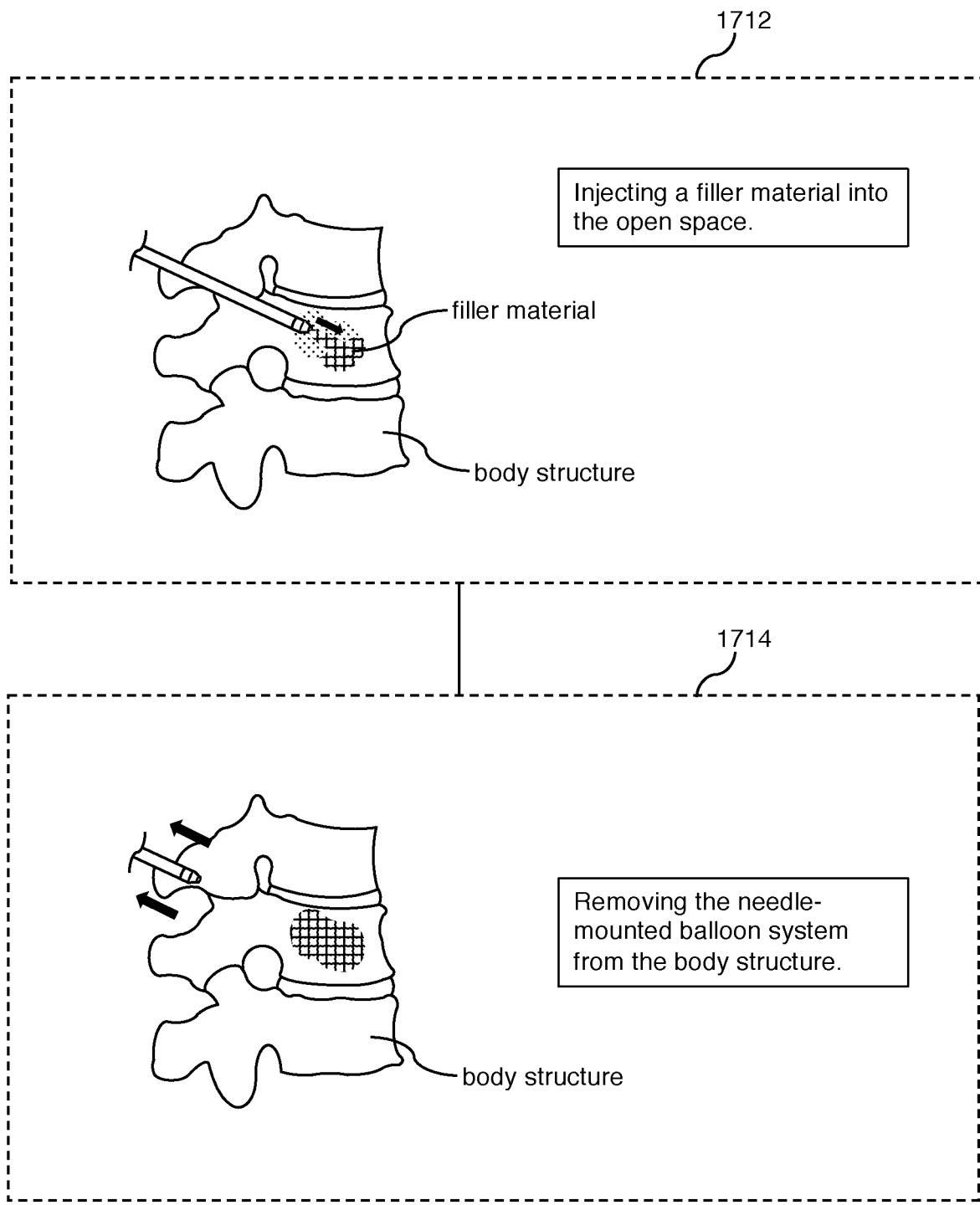

FIG. 17D shows injection of filler material into the open space, at step 1712. In many embodiments, the filler material is bone cement. The filler material may be injected via the injection port 134 shown in detail in FIG. 13. Similar to inflating the balloon 144, the filler material may be injected by pressurizing the source of the filler material to make it flow through the injection port 134. The open space may be partially or substantially completely filled by the filler material. In some embodiments, the balloon 144 is only partially deflated prior to injecting the filler material. Alternatively, the balloon 144 may be fully deflated prior to injecting the filler material.

The final step of the cementoplasty procedure, according to some embodiments, is to remove the needle-mounted balloon system 100 from the body structure as shown by step 1714. There may be a time gap between steps 1712 and 1714 to allow the filler material to harden, check for any issues with the procedure, and/or check to see if additional filler material needs to be injected. Any time gap and other and/or additional steps taken during the procedure may or may not occur at the discretion of the practitioner(s) performing the procedure.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

In addition, certain method, event, state, or process blocks may be omitted in some implementations. The methods, steps, and processes described herein are also not limited to any particular sequence, and the blocks, steps, or states relating thereto can be performed in other sequences that are appropriate. Multiple steps may be combined in a single block or state. The example tasks or events may be performed in serial, in parallel, or in some other manner. Steps or events may be added to or removed from the disclosed example embodiments. The example systems and components described herein may be configured differently than described. For example, elements may be added to, removed from, or rearranged compared to the disclosed example embodiments.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

Interpretation

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

To increase the clarity of various features, other features are not labeled in each figure. For example, elements like the cannula hub, stylet hub, cannula, etc. may be present in multiple figures but only explicitly labeled in one or two figures.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term "and/or" is used to avoid unnecessary redundancy.

The term "about" is used to mean approximately, and is not intended as a limiting term. For example, Claim 6 states that the distal-most portion of the cannula tube portion defines an outer diameter of about 0.134 inches. In this regard, "about" should be understood to mean the listed measurement +/−0.005. In statements listing a measurement to two decimal places, "about" should be understood to mean the listed measurement +/−0.05. In statements listing a measurement to no decimal places, "about" should be understood to mean the listed measurement to +/−0.5.

The terms "distal" and "proximal" are used frequently throughout this disclosure. The terms should be interpreted in the context of a thrombectomy procedure, where the distal access catheter, distal access catheter extension, guide catheter, and/or any other appropriate devices/systems are inserted near a patient's groin and navigated toward the patient's brain, where the thrombus resides. In this context, "distal" should be interpreted as indicating the direction toward the thrombus, and "proximal" should be interpreted as away from the thrombus. Said another way, "distal" is toward a patient's head and "proximal" is toward a patient's groin. It may also be helpful to understand "distal" as away from the practitioner performing the thrombectomy, and "proximal" as toward the practitioner.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

What is claimed is:

1. A needle-mounted balloon system, comprising:
   a cannula comprising:
      a handle;
      a cannula hub coupled within a housing of the handle;
      a cannula tube portion extending distally from the cannula hub, the cannula tube portion defining a lumen therethrough; and
      an expandable member coupled to the cannula tube portion, the expandable member being reconfigurable between a diametrically contracted configuration and a diametrically expanded configuration; and
   a stylet that is engageable with the cannula, the stylet comprising:
      a stylet hub detachably coupled to the handle; and
      a stylet needle extending distally from the stylet hub, wherein the stylet needle is slideably disposable within the lumen of the cannula tube portion, wherein, when the stylet is fully engaged with the cannula, a sharp distal tip portion of the stylet needle extends distally beyond the cannula tube portion, and wherein the expandable member is expandable when the stylet is disengaged from the cannula.

2. The needle-mounted balloon system of claim 1, comprising an outer sheath slideably coupled to the cannula tube portion, wherein the expandable member is located between the outer sheath and the cannula tube portion.

3. The needle-mounted balloon system of claim 2, further comprising an inflation port disposed on the cannula hub and an injection port disposed on the cannula hub, wherein the inflation port is in fluid communication with the expandable member and the injection port is in fluid communication with the lumen of the cannula tube portion.

4. The needle-mounted balloon system of claim 2, wherein the outer sheath is configured to retract and expose at least a portion of the expandable member when the stylet is disengaged from the cannula.

5. The needle-mounted balloon system of claim 2, wherein a distal-most portion of the cannula tube portion has a larger outer diameter than an outer diameter of the expandable member while the expandable member is in the diametrically contracted configuration.

6. The needle-mounted balloon system of claim 5, wherein the distal-most portion of cannula tube portion defines an outer diameter of about 0.134 inches.

7. The needle-mounted balloon system of claim 2, wherein an internal portion of the stylet needle is hollow.

8. The needle-mounted balloon system of claim 2, wherein an internal portion of the stylet needle is solid.

9. The needle-mounted balloon system of claim 2, wherein the distal tip portion of the stylet needle extends beyond the distal-most portion of the cannula tube portion a distance of about 0.24 inches.

10. The needle-mounted balloon system of claim 2, wherein the system defines a length of about 7 inches from the distal tip portion of the stylet needle to a proximal end of the handle.

11. The needle-mounted balloon system of claim 2, wherein the expandable member is a balloon that is diametrically symmetrical.

12. The needle-mounted balloon system of claim 2, wherein the expandable member is a balloon that is diametrically asymmetrical.

13. The needle-mounted balloon system of claim 2, wherein the expandable member is a balloon comprising dual-layers, wherein each layer is a 90AE balloon and the dual layers are coupled together via heat bonding.

14. A method for creating a space in a body structure and injecting a filler material into the space, the method comprising:
   inserting a distal end portion of a needle-mounted balloon system into the body structure, wherein the needle-mounted balloon system comprises;
      a cannula comprising:
         a handle;
         a cannula hub coupled within a housing of the handle;
         a cannula tube portion extending distally from the cannula hub, the cannula tube portion defining a lumen therethrough; and
         an expandable member coupled to the cannula tube portion, the expandable member being reconfigurable between a diametrically contracted configuration and a diametrically expanded configuration; and
      a stylet that is engageable with the cannula, the stylet comprising:
         a stylet hub detachably coupled to the handle; and
         a stylet needle extending distally from the stylet hub, wherein the stylet needle is slideably disposable within the lumen of the cannula tube portion, wherein, when the stylet is fully engaged with the cannula, a sharp distal tip portion of the stylet needle extends distally beyond the cannula tube portion, and wherein the expandable member is expandable when the stylet is disengaged from the cannula;
   reconfiguring the expandable member from the diametrically contracted configuration to the diametrically expanded configuration while the expandable member is in the body structure;
   reconfiguring the expandable member from the diametrically expanded configuration to the diametrically contracted configuration such that an open space remains in the body structure; and
   injecting the filler material into the open space.

15. The method of claim 14, further comprising retracting an outer sheath coupled to an external portion of the cannula in order to at least partially expose the expandable member.

16. The method of claim 15, further comprising prior to retracting the outer sheath, retracting the stylet needle through the lumen of the cannula.

17. The method of claim 16, wherein the body structure is bone and the filler material is bone cement.

18. The method of claim 16, wherein the stylet needle is retracted by turning a knob on the handle of the needle-mounted balloon system, wherein the knob is coupled to a proximal end of the stylet.

19. The method of claim 18, wherein turning the knob comprises a quarter turn.

20. The method of claim 18, wherein the outer sheath is retracted by moving at least one tab of the handle in a proximal direction, and wherein the at least one tab is exposed upon turning the knob, and the at least one tab is coupled to the outer sheath.

21. The method of claim 15, wherein reconfiguring the expandable member from the diametrically contracted configuration to the diametrically expanded configuration occurs in response to injecting at least one of saline and contrast dye into an inflation port disposed on the cannula hub.

* * * * *